(12) United States Patent
Jaber

(10) Patent No.: US 7,858,082 B2
(45) Date of Patent: Dec. 28, 2010

(54) METHOD OF STABILIZING PROTEINS

(75) Inventor: Amer Jaber, Gingins (CH)

(73) Assignee: Ares Trading S.A., Aubonne (CH)

( * ) Notice: Subject to any disclaimer, the term of this patent is extended or adjusted under 35 U.S.C. 154(b) by 740 days.

(21) Appl. No.: 11/597,982

(22) PCT Filed: May 27, 2005

(86) PCT No.: PCT/EP2005/052413

§ 371 (c)(1),
(2), (4) Date: Nov. 30, 2006

(87) PCT Pub. No.: WO2005/117948

PCT Pub. Date: Dec. 15, 2005

(65) Prior Publication Data

US 2007/0244299 A1 Oct. 18, 2007

(30) Foreign Application Priority Data

Jun. 1, 2004 (EP) .................................. 04076627

(51) Int. Cl.
*A61K 38/21* (2006.01)
*A61K 38/19* (2006.01)
*C07K 14/52* (2006.01)
(52) U.S. Cl. ....................... 424/85.6; 530/351; 424/85.1
(58) Field of Classification Search ........................ None
See application file for complete search history.

(56) References Cited

U.S. PATENT DOCUMENTS

| | | | |
|---|---|---|---|
| 4,432,895 A * | 2/1984 | Tarnowski | .................. 530/351 |
| 4,588,585 A | 5/1986 | Mark et al. | |
| 4,695,623 A | 9/1987 | Stabinsky | |
| 4,737,462 A | 4/1988 | Mark et al. | |
| 4,879,111 A | 11/1989 | Chong | |
| 4,897,471 A | 1/1990 | Stabinsky | |
| 4,904,584 A | 2/1990 | Shaw | |
| 4,959,314 A | 9/1990 | Mark et al. | |
| 4,965,195 A | 10/1990 | Namen et al. | |
| 5,017,691 A | 5/1991 | Lee et al. | |
| 5,116,943 A | 5/1992 | Koths et al. | |
| 5,541,293 A | 7/1996 | Stabinsky | |
| 5,917,021 A * | 6/1999 | Lee | .......................... 530/387.3 |
| 6,013,253 A | 1/2000 | Martin et al. | |

2002/0172661 A1 11/2002 Shirley et al.

FOREIGN PATENT DOCUMENTS

| EP | 0736303 B1 | | 3/1996 |
|---|---|---|---|
| WO | WO98/28007 | * | 7/1998 |
| WO | WO 99/55377 A3 | | 11/1999 |
| WO | WO 03/002152 A2 | | 1/2003 |
| WO | WO 2004/096263 A2 | | 11/2004 |

OTHER PUBLICATIONS

Derynck, R. et al. "Isolation and Structure of a Human Fibroblast Interferon Gene", *Nature*, Jun. 19, 1980, pp. 542-547, vol. 285.
Rubinstein, S. et al. "Convenient Assay for Interferons", *Journal of Virology*, Feb. 1981, pp. 755-758, vol. 37, No. 2.
Familletti, P. C. et al. "A Convenient and Rapid Cytopathic Effect Inhibition Assay for Interferon", *Methods in Enzymology*, 1981, pp. 387-394, vol. 78.
Shepard, H. M. et al. "A Single Amino Acid Change in IFN-$\beta_1$ Abolishes its Antiviral Activity", *Nature*, Dec. 10, 1981, pp. 563-565, vol. 294.
Mark, D. F. et al. "Site-Specific Mutagenesis of the Human Fibroblast Interferon Gene", *Proc. Natl. Acad. Sci.*, Sep. 1984, pp. 5662-5666, vol. 81, No. 18.
Pestka, S. "Interferon Standards and General Abbreviations", *Methods in Enzymology*, 1986, pp. 14-23, vol. 119.
Lam, X. M. et al. "The Effect of Benzyl Alcohol on Recombinant Human Interferon-$\gamma$", *Pharmaceutical Research*, 1997, pp. 725-729, vol. 14, No. 6.
Schuck, P. "Size-Distribution Analysis of Macromolecules by Sedimentation Velocity Ultracentrifugation and Lamm Equation Modeling", *Biophysical Journal*, Mar. 2000, pp. 1606-1619, vol. 78.
Wang, W. "Instability, Stabilization, and Formulation of Liquid Protein Pharmaceuticals", *International Journal of Pharmaceutics*, 1999, pp. 129-188, vol. 185.
Wang, Y.-C. J. et al. "Parenteral Formulations of Proteins and Peptides: Stability and Stabilizers", *Journal of Parenteral Science & Technology*, 1988, pp. S4-S26, vol. 42.

* cited by examiner

*Primary Examiner*—Christine J Saoud
*Assistant Examiner*—Jegatheesan Seharaseyon
(74) *Attorney, Agent, or Firm*—Saliwanchik, Lloyd & Saliwanchik

(57) ABSTRACT

A method of preparing a stabilized bulk solution of a monomeric protein is described, which consists in providing a bulk of monomeric protein in a buffer solution and adding an excipient to the bulk, wherein the excipient is selected from the group consisting of bacteriostatic agents, surfactants, isotonicity agents, amino acids, antioxidants and combinations thereof. Prefereably the monomeric protein is IFN-beta.

39 Claims, 10 Drawing Sheets

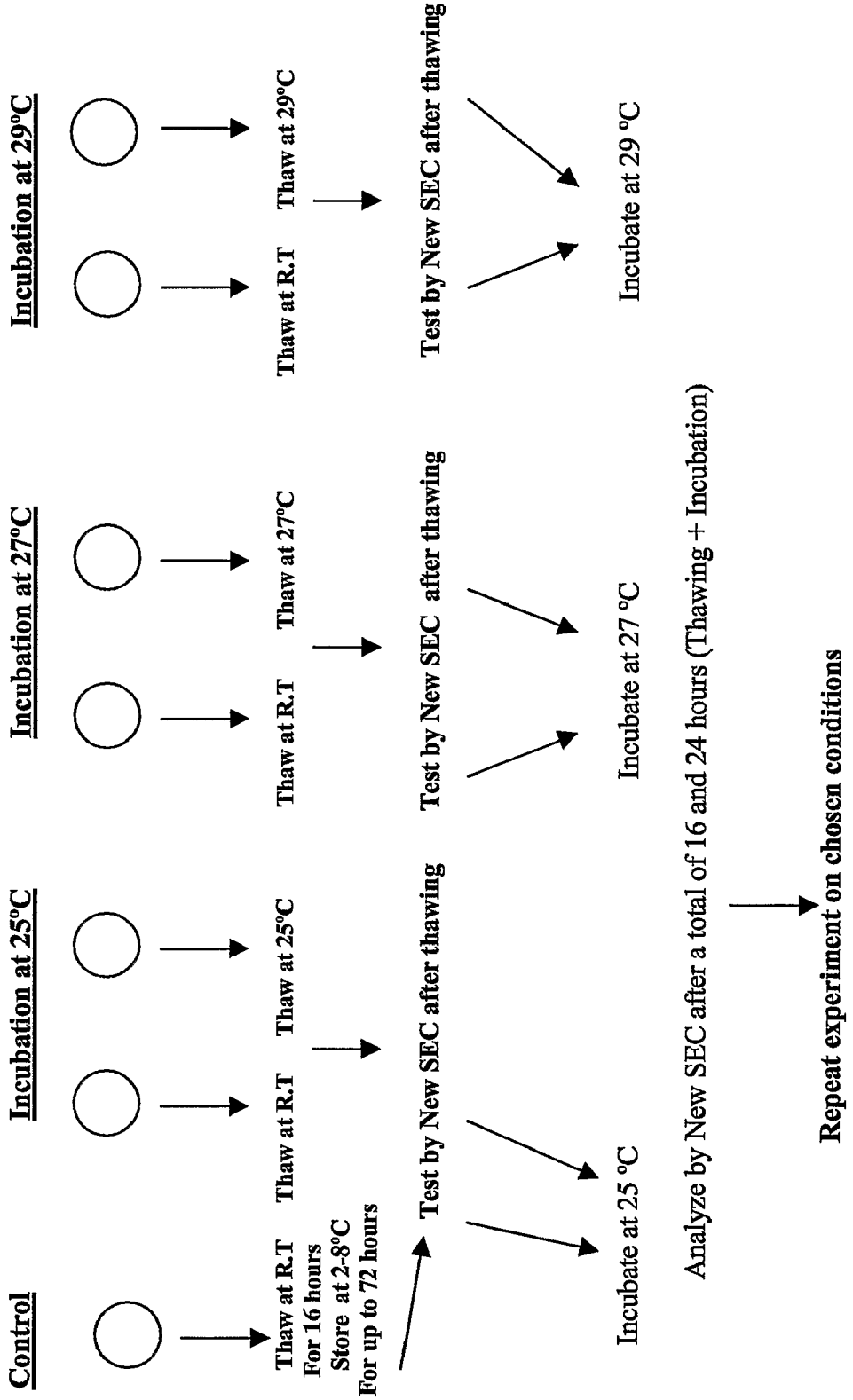
Figure 1 - Thermal Dissociation small lab scale procedure

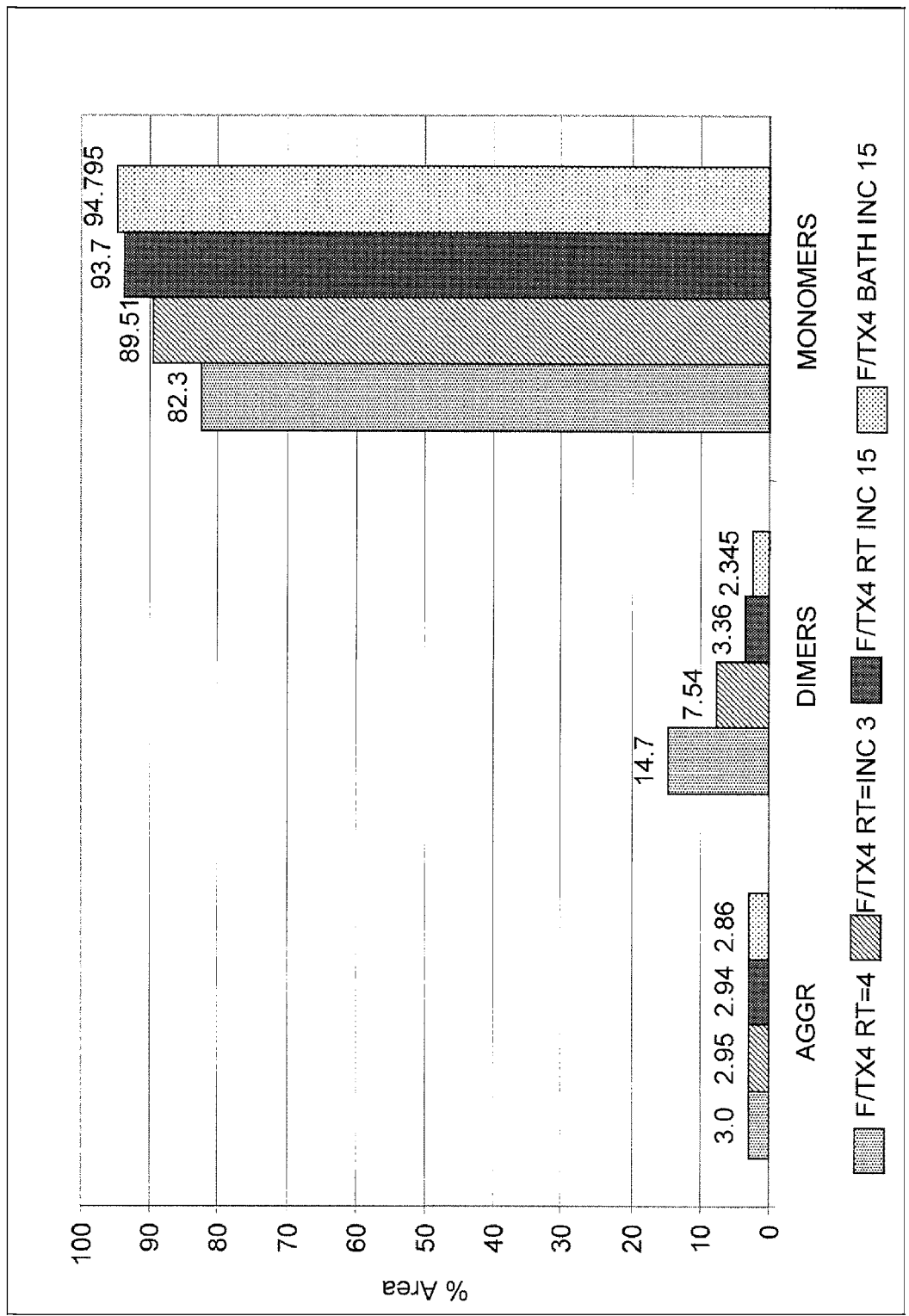
Figure 2 - SE-HPLC Results of 0.9ml Bulk Samples After 4f/T

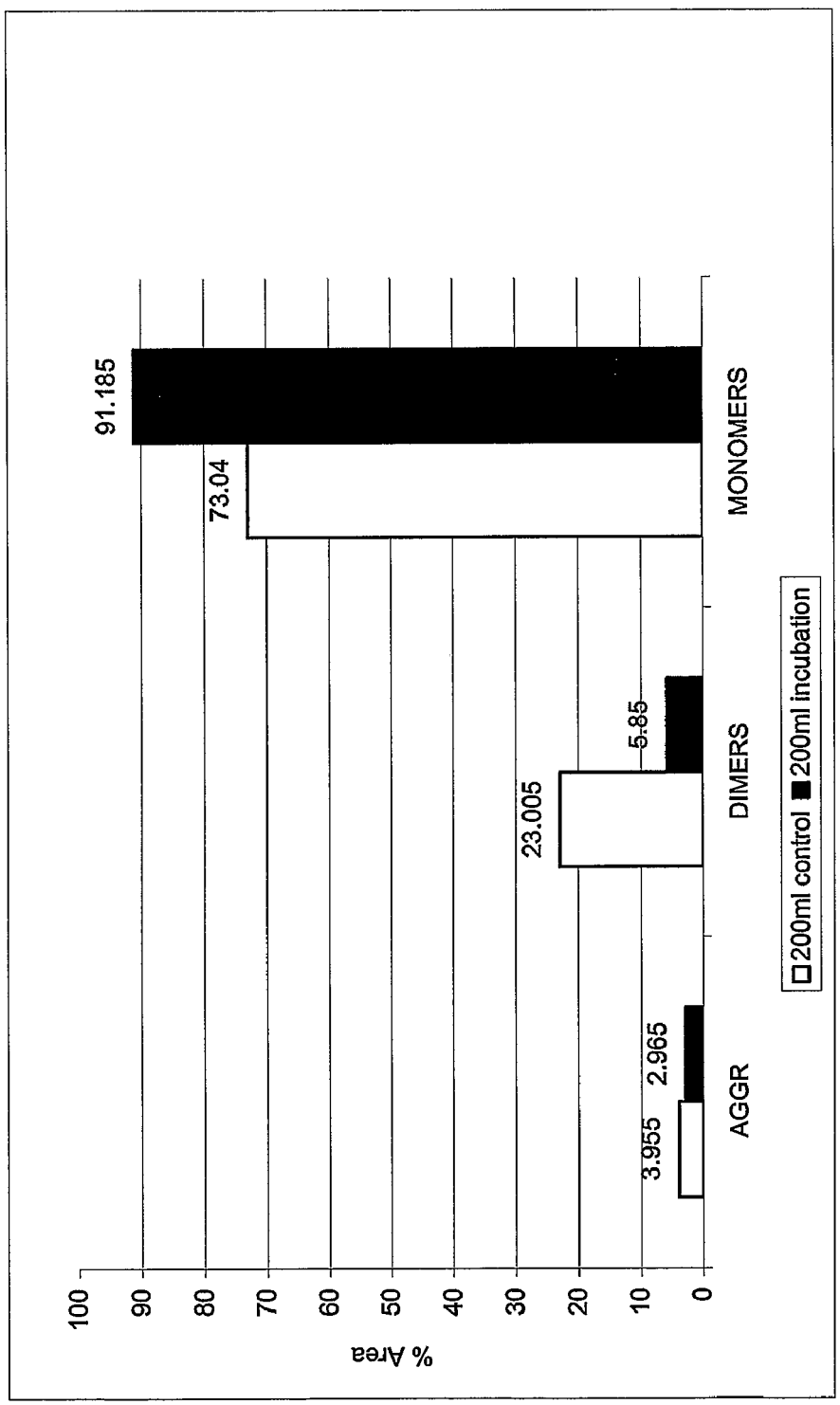
Figure 3 - SE-HPLC Results Of 200ml Bulk Samples After 2F/T

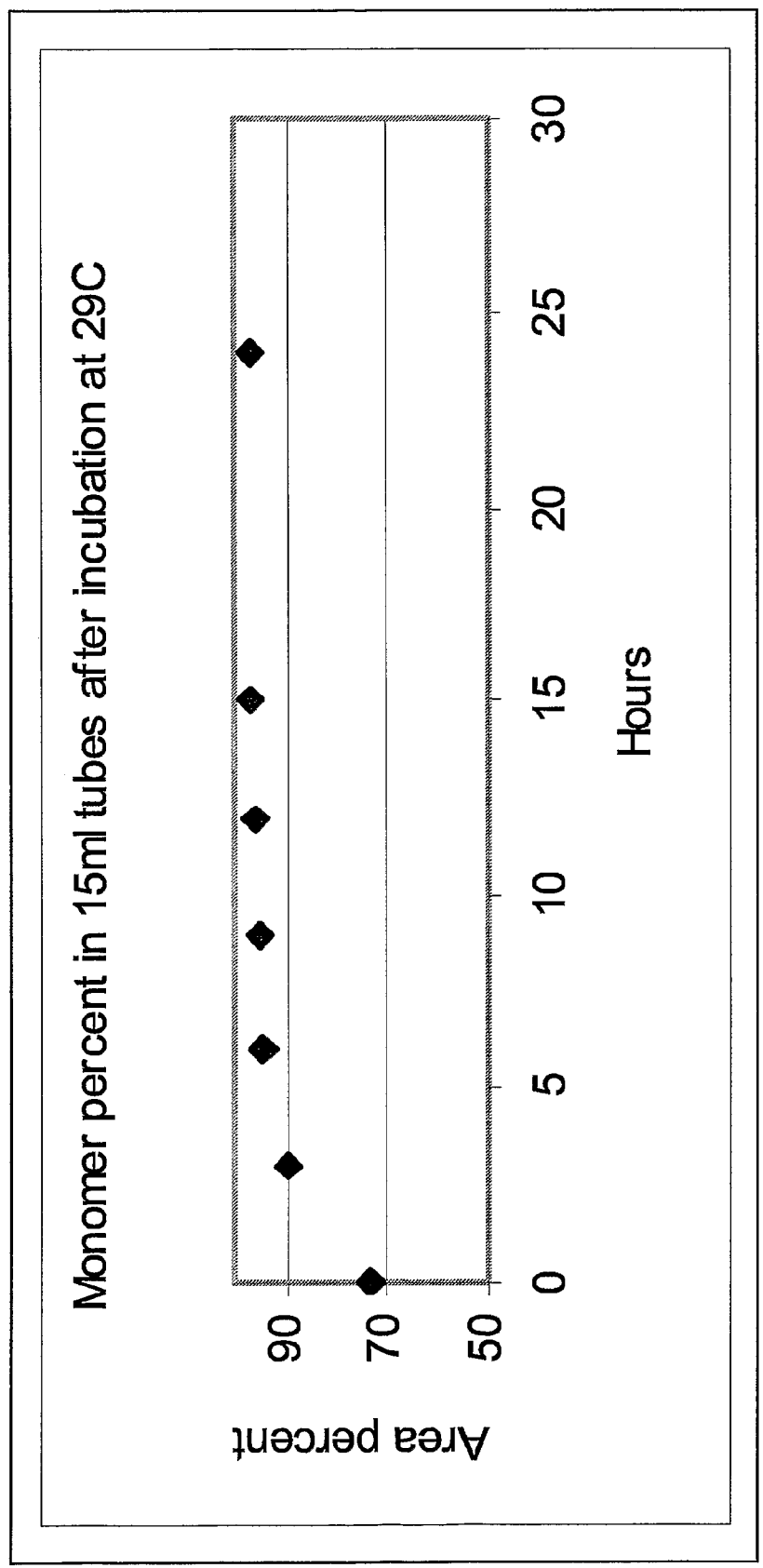
Figure 4 - Kinetics of thermal dissociation at labscale F/TX1. Monomer percentage over time.

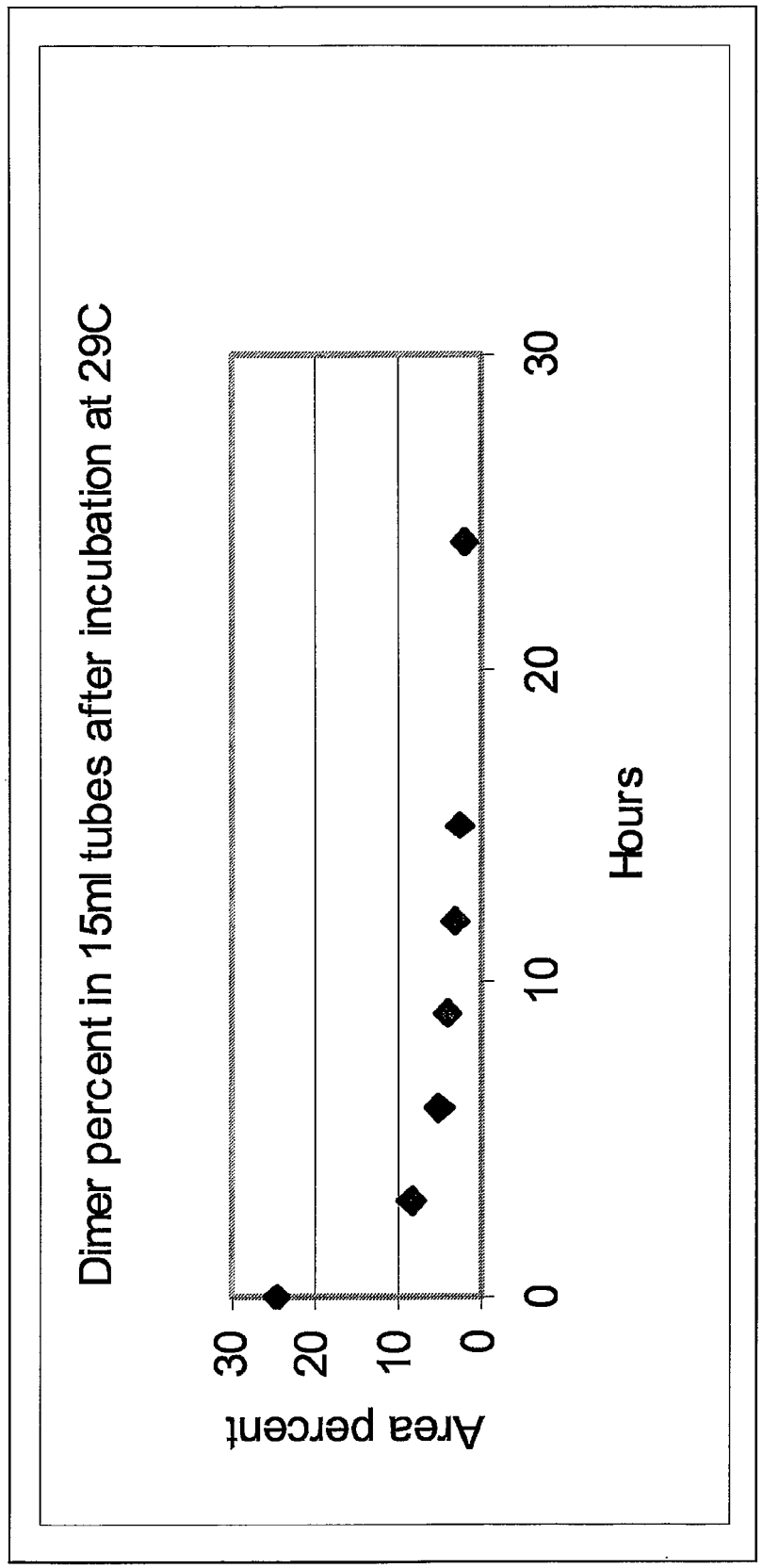
Figure 5 - Kinetics of thermal dissociation at labscale F/TX1. Dimer percentage over time.

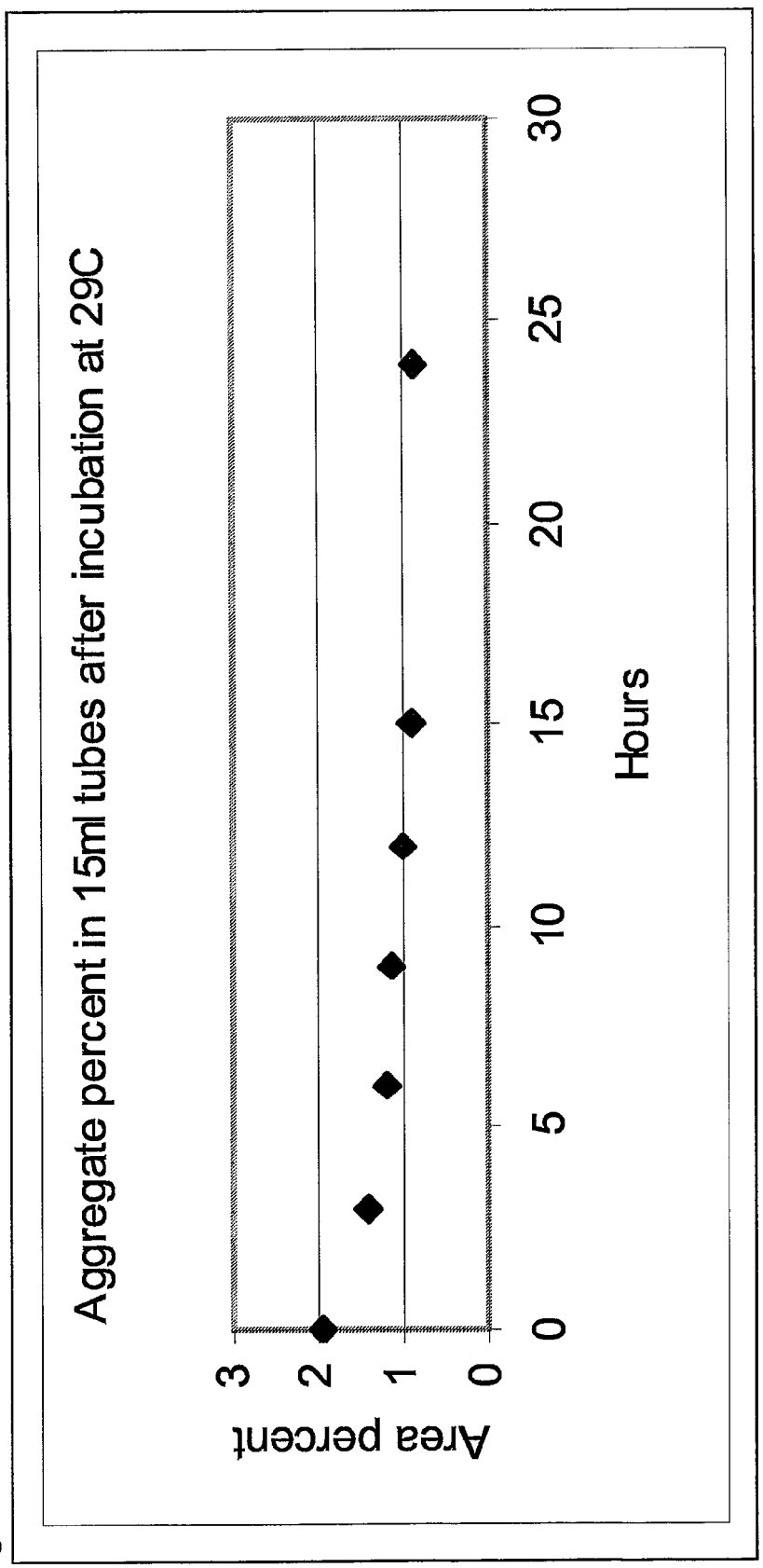
Figure 6 - Kinetics of thermal dissociation at labscale F/TX1. Aggregate percentage over time.

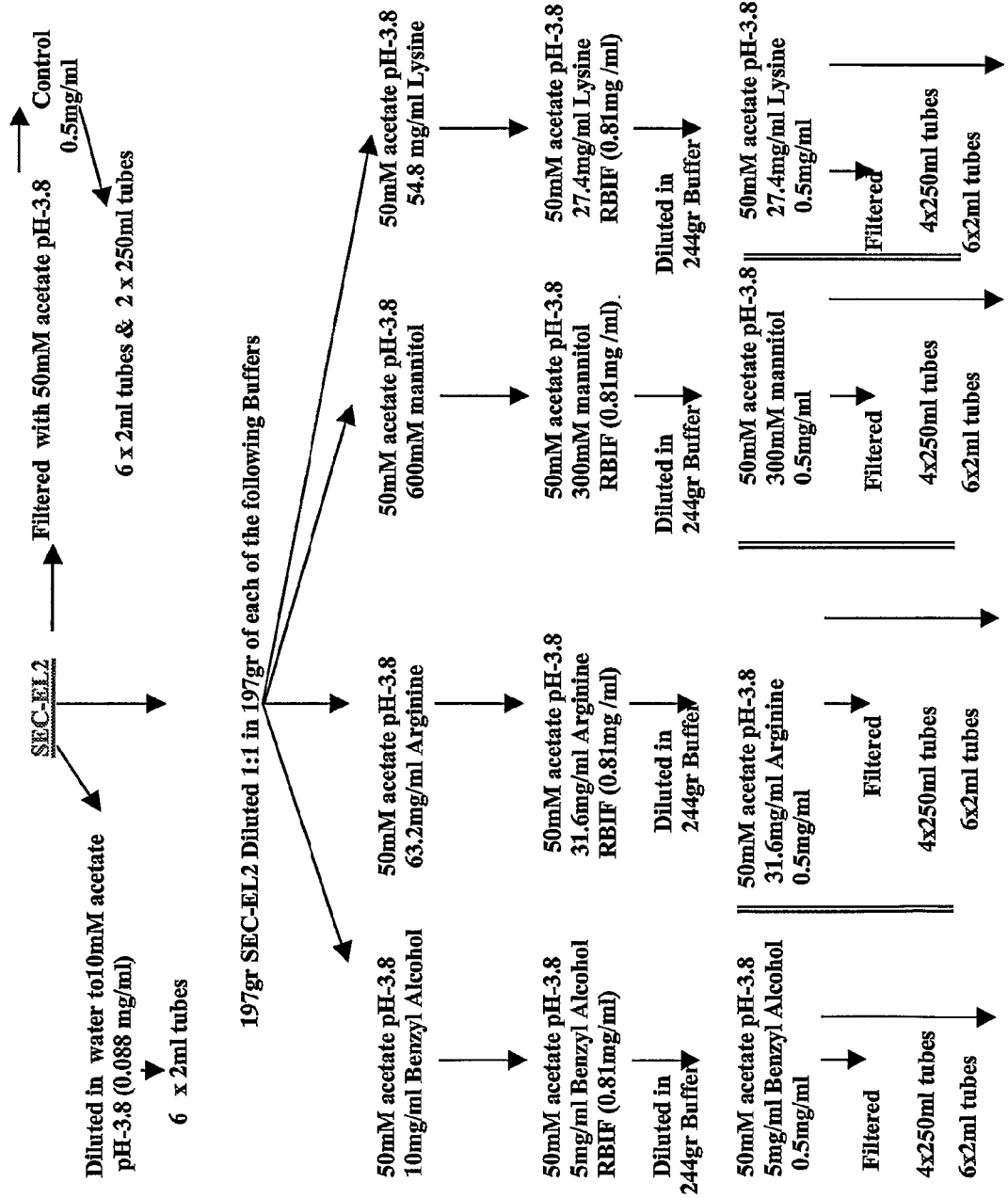
Figure 7 - Scheme of preformulation study for example 2

Figure 7 (cont.) - Scheme of preformulation study for example 2
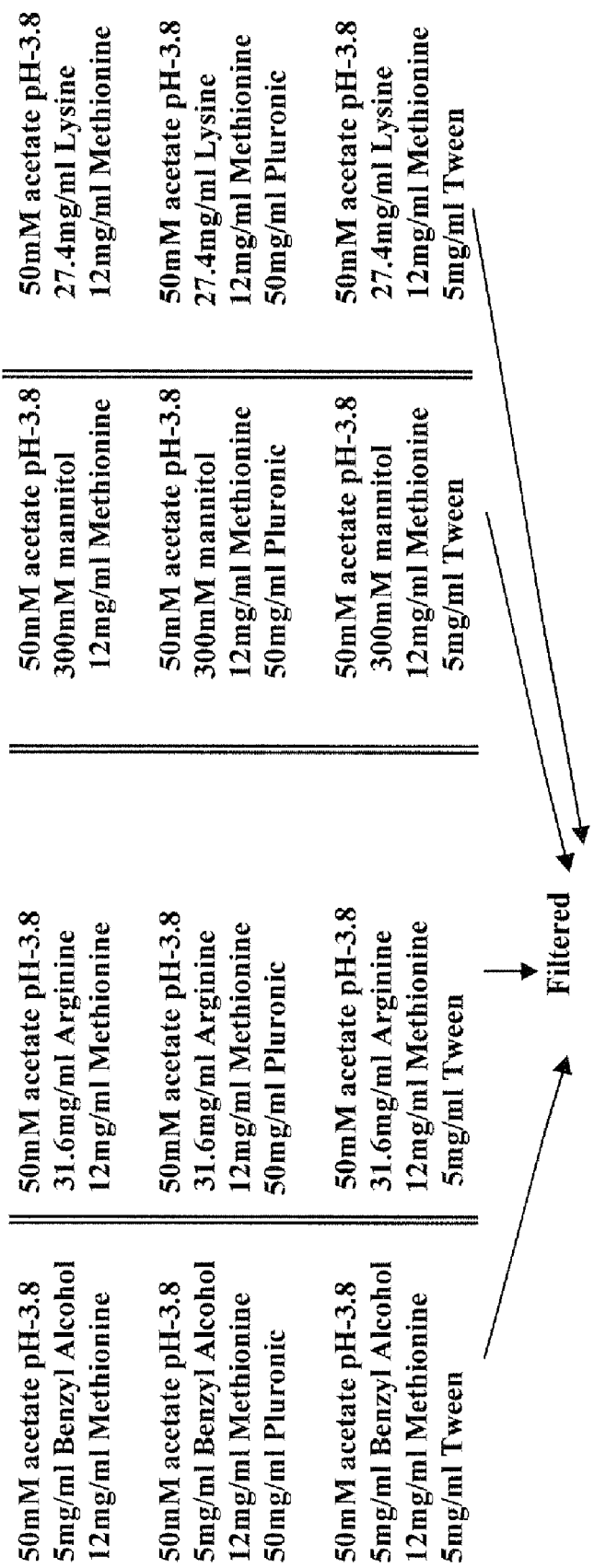

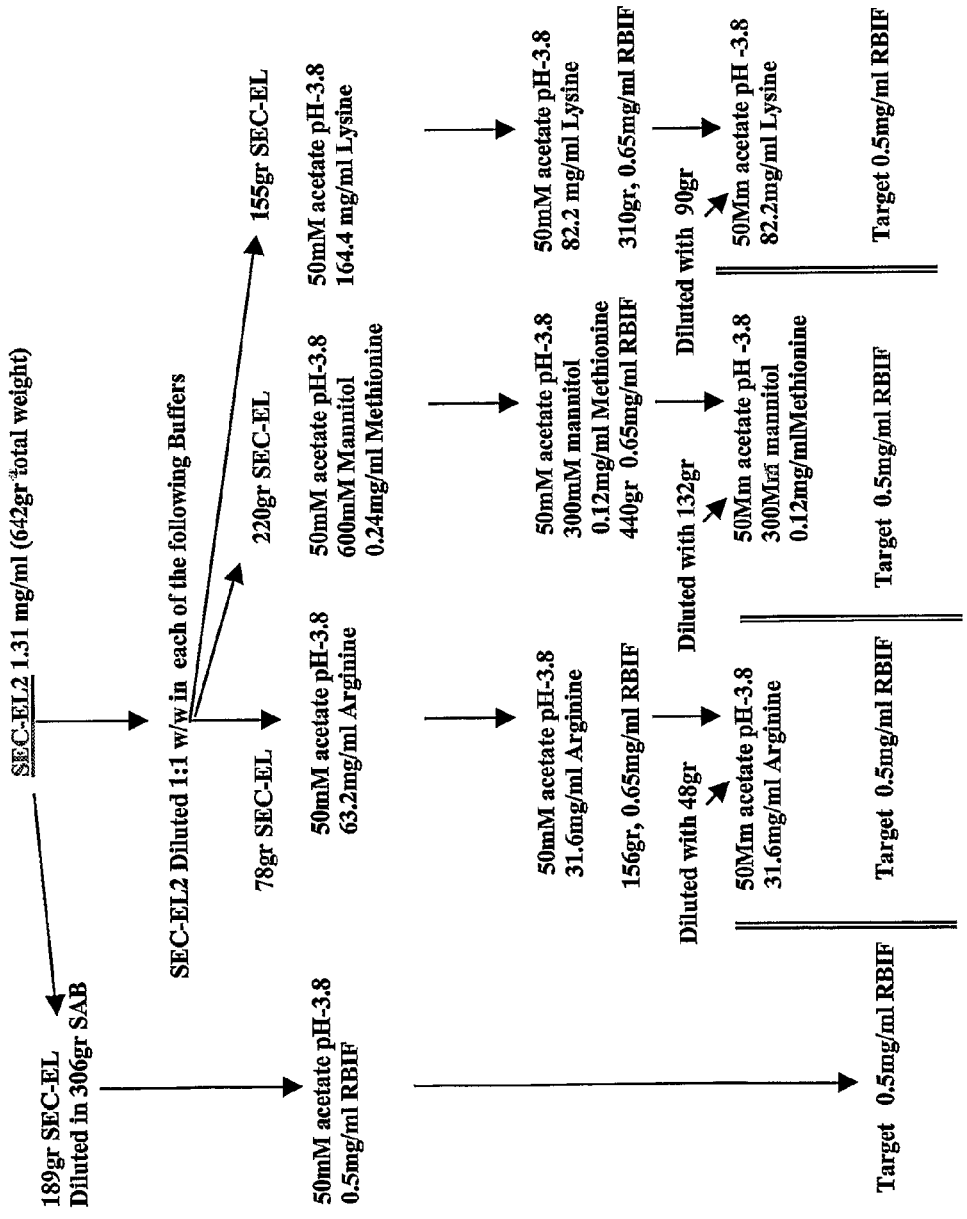
Figure 8 - Scheme of pre-formulation study for example 3

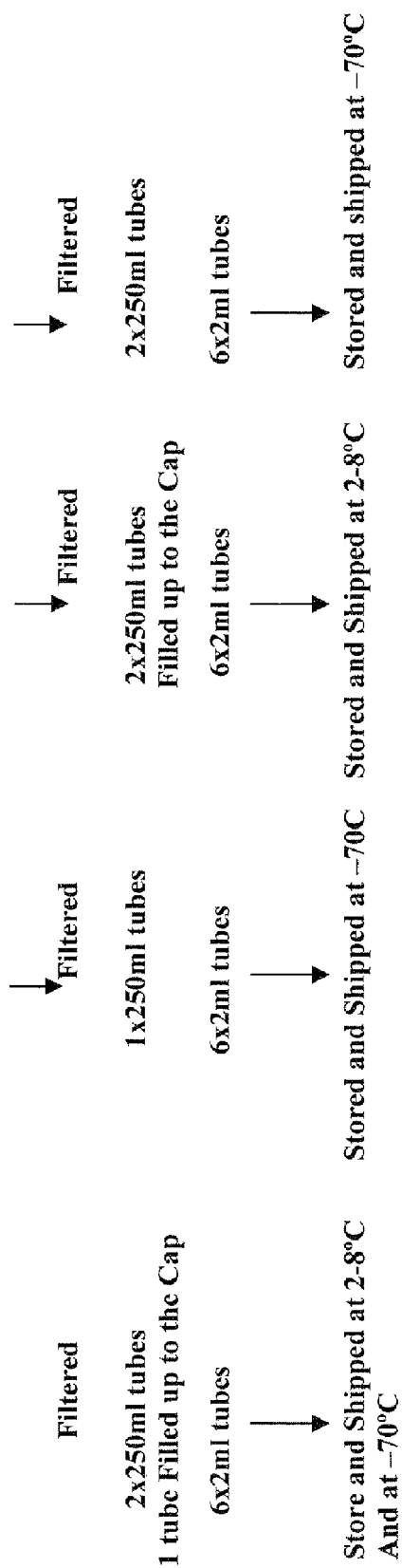
Figure 8 (cont.) - Scheme of pre-formulation study for example 3

METHOD OF STABILIZING PROTEINS

CROSS-REFERENCE TO RELATED APPLICATION

This application is the U.S. national stage application of International Patent Application No. PCT/EP2005/052413, filed May 27, 2005, the disclosure of which is hereby incorporated by reference in its entirety, including all figures, tables and amino acid or nucleic acid sequences.

FIELD OF THE INVENTION

The invention relates generally to a method of preparing a stabilized bulk solution of a monomeric protein by providing a bulk of monomeric protein in a buffer solution and by adding specific excipient(s) to the bulk solution.

BACKGROUND OF THE INVENTION

Interferons are cytokines, i.e. soluble proteins that transmit messages between cells and play an essential role in the immune system by helping to destroy microorganisms that cause infection and repairing any resulting damage. Interferons are naturally secreted by infected cells and were first identified in 1957. Their name is derived from the fact that they "interfere" with viral replication and production.

Interferons exhibit both antiviral and antiproliferative activity. On the basis of biochemical and immunological properties, the naturally-occurring human interferons are grouped into three major classes: interferon-alpha (leukocyte), interferon-beta (fibroblast) and interferon-gamma (immune). Alpha-interferon is currently approved in the United States and other countries for the treatment of hairy cell leukemia, venereal warts, Kaposi's Sarcoma (a cancer commonly afflicting patients suffering from Acquired Immune Deficiency Syndrome (AIDS)), and chronic non-A, non-B hepatitis.

Further, interferons (IFNs) are glycoproteins produced by the body in response to a viral infection. They inhibit the multiplication of viruses in protected cells. Consisting of a lower molecular weight protein, IFNs are remarkably non-specific in their action, i.e. IFN induced by one virus is effective against a broad range of other viruses. They are however species-specific, i.e. IFN produced by one species will only stimulate antiviral activity in cells of the same or a closely related species. IFNs were the first group of cytokines to be exploited for their potential anti-tumor and antiviral activities.

The three major IFNs are referred to as IFN-α, IFN-β and IFN-γ. Such main kinds of IFNs were initially classified according to their cells of origin (leukocyte, fibroblast or T cell). However, it became clear that several types might be produced by one cell. Hence leukocyte IFN is now called IFN-α, fibroblast IFN is IFN-β and T cell IFN is IFN-γ. There is also a fourth type of IFN, lymphoblastoid IFN, produced in the "Namalwa" cell line (derived from Burkitt's lymphoma), which seems to produce a mixture of both leukocyte and fibroblast IFN.

The interferon unit or International unit for interferon (U or IU, for international unit) has been reported as a measure of IFN activity defined as the amount necessary to protect 50% of the cells against viral damage. The assay that may be used to measure bioactivity is the cytopathic effect inhibition assay as described (Rubinstein, et al. 1981; Familletti, P. C., et al., 1981). In this antiviral assay for interferon about 1 unit/ml of interferon is the quantity necessary to produce a cytopathic effect of 50%. The units are determined with respect to the international reference standard for Hu-IFN-beta provided by the National Institutes of Health (Pestka, S. 1986).

Every class of IFN contains several distinct types. IFN-β and IFN-γ are each the product of a single gene.

The proteins classified as IFNs-α are the most diverse group, containing about 15 types. There is a cluster of IFN-α genes on chromosome 9, containing at least 23 members, of which 15 are active and transcribed. Mature IFNs-α are not glycosylated.

IFNs-α and IFN-β are all the same length (165 or 166 amino acids) with similar biological activities. IFNs-γ are 146 amino acids in length, and resemble the α and β classes less closely. Only IFNs-γ can activate macrophages or induce the maturation of killer T cells. These new types of therapeutic agents are sometimes called biologic response modifiers (BRMs), because they have an effect on the response of the organism to the tumor, affecting recognition via immunomodulation.

Human fibroblast interferon (IFN-β) has antiviral activity and can also stimulate natural killer cells against neoplastic cells. It is a polypeptide of about 20,000 Da induced by viruses and double-stranded RNAs. From the nucleotide sequence of the gene for fibroblast interferon, cloned by recombinant DNA technology, (Derynk et al. 1980) deduced the complete amino acid sequence of the protein. It is 166 amino acid long.

Shepard et al. (1981) described a mutation at base 842 (Cys→Tyr at position 141) that abolished its anti-viral activity, and a variant clone with a deletion of nucleotides 1119-1121.

Mark et al. (1984) inserted an artificial mutation by replacing base 469 (T) with (A) causing an amino acid switch from Cys→Ser at position 17. The resulting IFN-β was reported to be as active as the 'native' IFN-β and stable during long-term storage (−70° C.).

REBIF (Serono—recombinant human interferon-β), the latest development in interferon therapy for multiple sclerosis (MS), is interferon(IFN)-beta-1a, produced from mammalian cell lines. Its recommended International Non-proprietary Name (INN) is "Interferon beta-1a".

As with all protein-based pharmaceuticals, one major obstacle that must be overcome in the use of IFN-.beta. as a therapeutic agent, is the loss of pharmaceutical utility that can result from its instability in pharmaceutical formulations.

Physical instabilities that threaten polypeptide activity and efficacy in pharmaceutical formulations include denaturation and formation of soluble and insoluble aggregates, while chemical instabilities include hydrolysis, imide formation, oxidation, racemization, and deamidation. Some of these changes are known to lead to the loss or reduction of the pharmaceutical activity of the protein of interest. In other cases, the precise effects of these changes are unknown, but the resulting degradative products are still considered to be pharmaceutically unacceptable due to the potential for undesirable side effects.

The stabilization of polypeptides in pharmaceutical compositions remains an area in which trial and error plays a major role (reviewed by Wang (1999) Int. J. Pharm. 185:129-188; Wang and Hanson (1988) J. Parenteral Sci. Tech. 42:S3-S26). Excipients that are added to polypeptide pharmaceutical formulations to increase their stability include buffers, sugars, surfactants, amino acids, polyethylene glycols, and polymers, but the stabilizing effects of these chemical additives vary depending on the protein.

Current protein formulations employ the use of excipients to final preparations of proteins. However, these formulations remain in part unstable. In addition, proteins that are biologically active as monomers, i.e. monomeric proteins, have a tendency to polymerize and aggregate when stressed (e.g. temperature stress).

Consequently, there is a need for a method that improves the solubility of proteins and enhances stabilization of monomeric proteins particularly against aggregation and oligomerization, thereby enhancing their pharmaceutical utility.

SUMMARY OF THE INVENTION

In a first aspect, the invention provides a method of preparing a stabilized bulk solution of a monomeric protein, the method comprising the steps of:
- a) providing of a bulk of monomeric protein in a buffer solution, and
- b) adding an excipient to the bulk, wherein the excipient is selected from the group consisting of:
  - i) a bacteriostatic agent,
  - ii) a surfactant,
  - iii) an isotonicity agent,
  - iv) an amino acid,
  - v) an antioxidant,
  - vi) an isotonicity agent and an antioxidant,
  - vii) an isotonicity agent, an antioxidant and an amino acid,
  - viii) an amino acid and an antioxidant,
  - ix) an amino acid, an antioxidant and a surfactant,
  - x) a bacteriostatic agent and an antioxidant, and
  - xi) a bacteriostatic agent, an antioxidant and a surfactant.

In addition, the bulk protein can also be incubated at a specific temperature either before or after the method according to the first aspect of the invention.

In a second aspect, the invention provides a pre-formulated bulk protein obtained by the method according to the first aspect of the invention.

In a third aspect the invention provides a method for increasing and/or maintaining stability of a monomeric protein comprising the method of pre-formulation of the bulk of the protein according to the first aspect of the invention.

DESCRIPTION OF THE FIGURES

FIG. 1—Thermal Dissociation small lab scale procedure.

FIG. 1 refers to the thermal dissociation small lab scale procedure of example 1a related to the effect of incubation temperature and incubation time on bulk-interferon stabilization. FIG. 1 corresponds to table 4.

SE-HPLC Results of 0.9 ml Bulk Samples After 4 F/T.

FIG. 2 reports the Lab Scale Thermal Dissociation results at 29° C. after 4 F/T cycles of example 1b. The Y-axis refers to the area percentage. The X-axis refers to the detected forms of r-h IFN-beta 1a, i.e. aggregates, dimers or monomers. The first column of each detected form is the control and corresponds to a bulk pre-formulation which was thawed at RT for 2 hours and then stored at −4° C. The second column of each detected form corresponds to a bulk-pre-formulation which was thawed at RT for 2 hours and then incubated at 29° C. for 3 hours. The third column of each detected form corresponds to a bulk pre-formulation which was thawed at RT for 2 hours and then incubated at 29° C. for 15 hours. Last or fourth column of each detected form corresponds to a pre-formulation which was thawed in a bath and then incubated at 29° C. for 15 hours. FIG. 2 corresponds to table 11.

FIG. 3—SE-HPLC Results of 200 ml Bulk Samples After 2 F/T.

FIG. 3 reports the Lab Scale Thermal Dissociation results at 29° C. after 2 F/T cycles of example 1b. The Y-axis refers to the area percentage. The X-axis refers to the detected forms of r-h IFN-beta 1a, i.e. aggregates, dimers or monomers. The first column of each detected form is the control, and corresponds to a bulk pre-formulation which was thawed at RT for 7 hours and then stored at −4° C. The second column of each detected form corresponds to a bulk-pre-formulation which was thawed at RT for 7 hours and then incubated at 29° C. for 15 hours. FIG. 3 corresponds to table 12.

FIG. 4—Kinetics of thermal dissociation at labscale F/TX1. Monomer percentage over time.

FIG. 4 shows the monomer percentage of r-h IFN-beta 1a over time when incubated at 29° C. and following 1 F/T cycle. The Y-axis refers to the area percentage. The X-axis refers to the time in hours. Results of FIG. 4 are present in table 14.

FIG. 5—Kinetics of thermal dissociation at labscale F/TX1. Dimer percentage over time.

FIG. 5 shows the dimer percentage of r-h IFN-beta 1a over time when incubated at 29° C. and following 1 F/T cycle. The Y-axis refers to the area percentage. The X-axis refers to the time in hours. Results of FIG. 5 are present in table 14.

FIG. 6—Kinetics of thermal dissociation at labscale F/TX1. Aggregate percentage over time.

FIG. 6 shows the aggregate percentage of r-h IFN-beta 1a over time when incubated at 29° C. and following 1 F/T cycle. The Y-axis refers to the area percentage. The X-axis refers to the time in hours. Results of FIG. 6 are present in table 14.

FIG. 7—Scheme of preformulation study for example 2.

FIG. 7 represents the scheme of the study of example 2 which is focused on minimization of oligomerization of r-h IFN-beta 1a during manufacturing steps from the SEC-EL fraction to the final dosage form (FDF) storage in order to provide a stabilized bulk interferon-beta. The scheme is also described under section 6.2 of example 2.

FIG. 8—Scheme of preformulation study for example 3.

FIG. 8 represents the scheme of the study of example 3 aimed at minimizing oligomerization of r-h IFN-beta 1a and which uses two different methods, velocity ultracentrifugation and SE-HPLC, for the measurement of r-h IFN-beta 1a monomer level after stabilization of the bulk IFN-beta. The scheme is also described under sections 6.1 and 6.2 of example 3.

DETAILED DESCRIPTION OF THE INVENTION

The present invention is directed to a method of preparing a stabilized bulk solution of a monomeric protein, the method comprising the steps of:
- a) providing of a bulk of monomeric protein in a buffer solution, and
- b) adding an excipient to the bulk, wherein the excipient is selected from the group consisting of:
  - i) a bacteriostatic agent,
  - ii) a surfactant,
  - iii) an isotonicity agent,
  - iv) an amino acid,
  - v) an antioxidant,
  - vi) an isotonicity agent and an antioxidant,
  - vii) an isotonicity agent, an antioxidant and an amino acid,
  - viii) an amino acid and an antioxidant,
  - ix) an amino acid, an antioxidant and a surfactant,
  - x) a bacteriostatic agent and an antioxidant, and
  - xi) a bacteriostatic agent, an antioxidant and a surfactant.

It has in fact been found by the Applicant that, if stabilization is performed by the addition to the bulk protein of one or more excipients as described in detail in this patent application stability is conferred starting from the moment that one or more excipients are added to the bulk protein until final disposal of the formulation containing the protein, e.g. final uptake by a patient. Thus, stabilization doesn't occur only at storage stage but throughout the various stages that the protein may face during its lifetime until its disposal, i.e. before, during and after storage. The method of the present invention is thus able to counteract the various stresses that the protein or the protein formulation may endure during its lifetime. Thus, stabilization occurs not only at manufacturing but also at transportation, storage and delivery processes.

The invention also encompasses the stabilized bulk obtained by the method of the present invention, also called pre-formulated bulk.

The term "pre-formulations" herein refers to formulations containing a bulk monomeric protein. Stability of these pre-formulations is not only conferred in terms of lowering aggregation and oligomerization, but also include other types of deleterious processes such as oxidation, deamidation, etc. As such, the present invention also encompasses any other types of processes, as long as these processes have an impact on stability of the monomeric protein.

The term "during storage" is referred to a formulation or composition that, once prepared, is not immediately administered to a subject. Rather, following preparation, it is packaged for storage, either in a liquid form or other form suitable for administration to a subject.

By "dried form" is intended the formulation or composition which is dried either by freeze drying, spray drying, or air drying. Aggregate or oligomer formation by a monomeric protein or any other constituents of the pharmaceutical formulation can adversely affect biological activity of the monomeric protein, resulting in loss of therapeutic efficacy of the pharmaceutical formulation. Furthermore, aggregate or oligomer formation may cause others problems such as blockage of tubing, membranes, or pumps when the monomeric protein-containing pharmaceutical composition is administered using an infusion system.

The term "stability" refers to the relative temporal constancy of a protein activity such as anti-viral activity and/or protein structure and has by necessity a functional definition. The term "stability" also refers to the physical, chemical, and conformational stability of preformulations of interferon of the present invention (including maintenance of biological potency). Instability of a protein pre-formulation may be caused by chemical degradation or aggregation of the protein molecules to form higher order polymers, deglycosylation, modification of glycosylation, oxidation or any other structural modification that reduces at least one biological activity of a monomeric protein included in the present invention.

A "stable" preformulation, is one wherein the degree of degradation, modification, aggregation, loss of biological activity and the like, of proteins therein is acceptably controlled, and does not increase unacceptably with time.

The terms "stabilized" refer to a monomeric protein or a formulation containing a monomeric protein of the present invention which shows increased or/and maintained stability relative to monomeric proteins or formulations prepared in the absence of an excipient as disclosed herein added to the bulk monomeric protein or a formulation containing the monomeric protein.

As used herein, the term "stabilizing" is used interchangeably with "reducing or/and preventing protein aggregation" and/or "reducing or/and preventing protein oligomerisation" and/or "reducing or/preventing aggregates formation" and/or "reducing and/or preventing polymerization" and/or "reducing and/or preventing oxidation" and/or "reducing and/or preventing micelle(s) formation" and/or "reducing and/or preventing deamidation" and/or "reducing and/or preventing the deleterious effect of any kind of process on a monomeric protein or formulation containing the monomeric protein".

The terms "monomer" or "monomeric" refers to a molecule having only a single peptide chain.

The terms "bulk protein" or "bulk of the protein" or "bulk monomeric protein" or "bulk of the monomeric protein" refer herein to the state of a protein or monomeric protein which has already been subjected to the purifications steps of the manufacturing process, but not yet to the final formulations steps, which allow to prepare the "final dosage form" (FDF) or "pharmaceutical composition" as finally packaged and distributed for sales. Thus a bulk of a recombinant protein is herein considered to be the product resulting at the end of the purification process, but before that this product is subjected to the final formulation steps. In other words the method of the present invention can be considered as comprising a pre-formulation step, which allows to obtain a pre-formulated bulk, which by the following addition of further excipients, will produce the final dosage form or pharmaceutical composition. Usually, the pre-formulated or non-formulated bulk is stored before that the final formulation is prepared, but not necessarily. If stored in a frozen state, the bulk protein is usually thawed, filtered and then subject to the final formulation steps, but not necessarily.

According to a specific embodiment of the present invention in the case in which the protein is recombinant-human interferon-beta 1a (r-hIFN-beta 1a), a stabilizing excipient is added to the eluate of final chromatographic step, which can be for example a size exclusion chromatography (SEC), herein referred to as "SEC-EL" or "SEC-EL2", either before being subjected to a filtration step or just after a filtration step (see Examples). In this case, the SEC represents the final step of the purification procedure. In other purifications procedures, other chromatography techniques or separations methods may be used at the final step, or other purification methods may be applied which do not rely on separation methods as a final purification step; this should by no means limit the scope of the present invention as defined by the term "bulk protein". As long as the stabilizing excipient is added after the purification procedure, whatever the purification method(s) may be, it is encompassed by the present invention. In addition, the stabilizing excipients mentioned in the present invention can also be further added to a final formulation (FDF). Thus, the excipients comprised in a FDF can correspond to those that were added to the bulk preformulation, but not necessarily.

An "oligomeric protein" or "oligomer" as used herein, refers to a multisubunit protein having two or more polypeptide chains. An "oligomeric protein" is sometimes referred to as a protein where two or more of its units are identical polypeptide chains. Three types of oligomers can at least be distinguished:

Rapidly-reversible non-covalent small oligomers (dimer, trimer, tetramer, etc.)

Irreversible non-covalent oligomers

Covalent oligomers (e.g. disulfides)

"Multimeric protein" is descriptive of a protein composed of several subunits. A "subunit" refers to one of the identical or non-identical protein molecules that make up a multimeric protein.

"Oligomerization" refers to the chemical process of creating oligomers from larger or smaller molecules. "Oligomerization" is also referred to as the process of converting a monomer or a mixture of monomers into an oligomer. The term "oligomerization" also refers to the formation of multimers of individual protein molecules through non covalent or covalent interaction. Oligomerization can be reversible or irreversible.

The term "polymerisation" describes chemical reactions that produce polymers by repeated combination of monomers to make long or large molecules or the process of converting a monomer or a mixture of monomers into a polymer.

The term "aggregation" refers to the formation of higher-molecular-mass species mainly due to non-covalent adherence of smaller species. Especially for proteins, aggregation is a form of denaturation in which non-polar surfaces of secondary structures, e.g. those of α-helices and β-sheets that normally form intramolecular interactions and are buried within the interior of the protein, are allowed to interact intermolecularly and to form multimolecular forms that are sometimes insoluble. The terms "insoluble" versus "soluble" are sometimes referred to as respectively "irreversible" versus "reversible". Aggregates can also be defined as large oligomeric protein associations (for example more than 10-mer). 'Aggregates' could be reversible if non-covalent.

The present invention should not be limited by the definitions "aggregation", "aggregate(s)", "oligomer(s)", "multimer(s)", "oligomerization", "multimerisation", "multimeric", "oligomeric", "polymerization", whatever the definitions may be. Thus, the scope of the present invention should not be limited by those terms or by any theory surrounding them. The important issue is that "aggregates" and "oligomers" can be distinguished one another by detection methods (e.g. SE-HPLC), usually by separated distinguishable signals, e.g. by separated peaks; each of the peak corresponding either to aggregates or oligomers. Likewise, the monomeric form of the protein corresponds to a precise unique determined peak.

The term "buffer" or "physiologically-acceptable buffer" refers to solutions of compounds that are known to be safe for pharmaceutical or veterinary use in formulations and that have the effect of maintaining or controlling the pH of the formulation in the pH range desired for the formulation. Acceptable buffers for controlling pH at a moderately acidic pH to a moderately basic pH include, but are not limited to, such compounds as phosphate, acetate, citrate, arginine, TRIS, and histidine. "TRIS" refers to 2-amino-2-hydroxymethyl-1,3,-propanediol, and to any pharmacologically acceptable salt thereof. Preferable buffers are acetate buffers with saline or an acceptable salt.

An "isotonicity agent" is a compound that is physiologically tolerated and imparts a suitable tonicity to a formulation to prevent the net flow of water across cell membranes that are in contact with the formulation. Compounds such as glycerin, are commonly used for such purposes at known concentrations. Other suitable isotonicity agents include, but are not limited to, amino acids or proteins (e.g., glycine or albumin), salts (e.g., sodium chloride), and sugars (e.g., dextrose, mannitol, sucrose and lactose). Preferably the isotonicity agent is mannitol.

The term "antioxidant" refers to a compound that prevents oxygen or oxygen-derived free radicals from interacting with other substances. Antioxidants are among a number of excipients commonly added to pharmaceutical systems to enhance physical and chemical stability. Antioxidants are added to minimize or retard oxidative processes that occur with some drugs or excipients upon exposure to oxygen or in the presence of free radicals. These processes can often be catalyzed by light, temperature, hydrogen on concentration, presence of trace metals or peroxides. Sulfites, bisufites, thiourea, methionine, salts of ethylenediaminetetraacefic acid (EDTA), butylated hydroxytoluene (BHT), and butylated hydroxy anisole (BHA) are frequently used as antioxidants in drugs. Sodium EDTA has been found to enhance the activity of antioxidants by chelating metallic ions that would otherwise catalyze the oxidation reaction. Most preferred antioxidant is methionine. Antioxidants are herein also referred to as stabilizers.

Methionine can be present either in its free base form or in its salt form. Any stereoisomer (i.e., L, D, or DL isomer) of methionine may be used in the present method or formulation of the invention so long as methionine is present in its free base form or its salt form. Preferably, the L-stereoisomer is used. Analogues of methionine may also be used in the present formulation of the invention. The term "methionine analogue" refers to a derivative of the naturally occurring methionine. The methionine analogues can also be used in the present formulation in either their free base form or their salt form.

Increased and/or maintained stability with addition of antioxidants (e.g. methionine) occurs in a concentration dependent manner. That is, increasing concentrations of antioxidants lead to increased and/or maintained stability of the formulation containing interferon-beta of the present invention when that formulation containing interferon-beta normally exhibits oxidation or aggregate/oligomer formation in the absence of the antioxidant. Determination of the amount of an oxidant (e.g. methionine) to be used in the present formulation of the invention, in order to decrease oxidation or oligomer/aggregate formation, can readily be determined without undue experiment using methods generally known to one of skill in the art.

The term "bacteriostatic" refers to a compound or compositions added to a formulation to act as an anti-bacterial agent. A preserved interferon-containing formulation of the present invention preferably meets statutory or regulatory guidelines for preservative effectiveness to be a commercially viable multi-use product. Examples of bacteriostatics include phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal. Preferably the bacteriostatic agent is benzyl alcohol. Benzylalcohol is also referred herein as a stabilizer.

The term "surfactant" refers to a soluble compound that reduces the surface tension of liquids, or reduces interfacial tension between two liquids or a liquid and a solid, the surface tension being the force acting on the surface of a liquid, tending to minimize the area of the surface. Surfactants have sometimes been used in pharmaceutical formulations, including delivery of low molecular mass drugs and polypeptides, in order to modify the absorption of the drug or its delivery to the target tissues. Preferably, the surfactant is TWEEN 20 or a poloxamer. More preferably, the surfactant is Poloxamer 188. Even more preferably, the surfactant is TWEEN 20.

The term "amino acid" refers to an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. Preferred amino acids to use in the present method or formulation of the present invention are those carrying a charged side chain, such as arginine, lysine, aspartic acid, and glutamic acid. More preferably, the amino acids are lysine and arginine. Even more preferably, the amino acid is lysine. Any stereoisomer (i.e., L, D, or DL isomer) of a particular amino acid, or combinations of these stereoisomers, may be used in the present method or formulation of the invention so long as the particular amino acid is present in its free base form or its salt form. Preferably, the L-stereoisomer is used. Analogues of these preferred amino acids might also be used in the present method or formulation of the invention. The term "amino acid analogue" refers to a derivative of the naturally occurring amino acid. Suitable arginine analogues include for example, aminoguanidine and N-monoethyl L-arginine. As with the preferred amino acids, the amino acids analogues are used in the present method or formulation in either their free base form or their salt form. Amino acids are herein also referred to as stabilizers.

The amino acid(s) used in the present method or formulation of the invention protects the therapeutically active polypeptide against various stresses thereby increasing or/and maintaining stability of the monomeric protein or formulation containing the monomeric protein during the lifetime of the monomeric protein (before, during and after storage). Herein, the term "stress" includes but is not limited to heat, freezing, pH, light, agitation, oxidation, dehydration, surfaces, shear, freeze/thawing, pressure, heavy metals, phenolic compounds, denaturants, etc. The term stress encompasses any factor that modulates (i.e. reduces, maintains or increases) the stability of a (monomeric) protein or a formulation containing the (monomeric) protein. Increased and/or maintained stability with addition of an amino acid occurs in a concentration dependent manner. That is, increasing concentrations of amino acid lead to increased and/or maintained stability of a monomeric protein or a formulation containing a monomeric protein of the present invention when that monomeric protein or formulation containing that monomeric protein normally exhibits aggregate or oligomer formation in the absence of the amino acid. Determination of the amount of a particular amino acid to be used in the present method or formulation of the invention to decrease oligomer or aggregate formation thereby increasing monomeric protein stability, and thus increasing stability of the formulation during the entire lifetime of the monomeric protein, can readily be determined for any particular monomeric protein of interest without undue experiment using methods generally known to one of skill in the art.

"Frozen storage" refers to freezing and maintaining a previously aqueous monomeric protein preparation at a temperature below 0° C., preferably −20° C. or lower, more preferably −70° C.

"Freeze/thaw cycles" or "freeze/thaw manipulations" refer to known techniques for using a protein sample in frozen storage, wherein the temperature of the sample is raised to a level which will restore its aqueous state for a sufficient period of time to permit use of the Rampie, followed by freezing to a temperature below 0° C. and return to frozen storage, preferably at a temperature of −20° C. or lower, more preferably −70° C.

The purpose of the present invention is to counteract at least both aggregation and oligomerization processes (the invention is not limited to these processes) not only of the monomeric protein but also of other agents, ingredients or compounds that are also added to the bulk protein according to the present invention. Thus, the present invention is able to confer stability (e.g. by reducing and/or inhibiting formation of oligomers as well as aggregates) to all the compounds, agents (e.g. bacteriostatic agents, isotonicity agents), proteins, surfactants, excipients, which are added to the bulk according to the present invention and which will be included in the final dosage form or pharmaceutical composition of the protein at issue. In other words, stabilization is conferred not only to the (monomeric) protein but also to the "Whole" formulation containing the (monomeric) protein. Aggregation can not only compromise biological activity but also lead to injection site reactions and immunogenecity through development of neutralizing antibodies (NAbs).

The present examples clearly show that addition of particular excipients to a bulk monomeric protein formulation can significantly increase the stability and solubility of the monomeric protein formulation by preventing and/or inhibiting the formation of polypeptide aggregates or oligomers during frozen storage or/and repeated freeze/thaw cycles. In addition, the present invention shows that thermal dissociation is effective in conferring stability to a (monomeric) protein or a formulation containing the (monomeric) protein.

The term "thermal dissociation" herein refers to the process by which proteins that are in the form of multimers are converted or dissociated into a reduced multimeric-form or to a monomeric form by the action of temperature (e.g. dimers of a protein are converted to monomers when subject to a specific temperature). The protein in the formulation is present in multiple multimeric forms (dimeric, trimeric, etc.). Thermal dissociation is thus effective in converting or dissociating all multimeric forms to reduced multimeric forms or monomeric forms. The present invention shows that there's a correlation between temperature and dissociation of the multimers. When subject to thermal dissociation, a formulation will comprise less multimeric forms and increased monomeric forms compared to one which was not subject to thermal dissociation. Preferably, thermal dissociation converts all multimeric forms into monomeric forms. The temperature can be immediately set at a fixed temperature or let for gradual increase until a specific temperature is attained. In addition, the present invention demonstrates that the duration of the thermal dissociation is effective in stabilizing the (monomeric) protein or formulation containing the (monomeric) protein. The present invention shows that there's a correlation between duration of thermal dissociation and dissociation of the -mers. Examples indicate that thermal dissociation is mostly effective during the first hours of thermal dissociation, until reaching a certain point where duration becomes ineffective. Thermal dissociation is protein specific. Setting adequate parameters like temperature and duration for a particular protein to achieve optimal thermal dissociation can easily be performed by the man of art using conventional techniques.

Numerous analytical methods are known by the man of art to determine degradation products such as aggregation, oxidation, deamidation, cleavage, surface adsorption, surface denaturation, cyclic imdide formation, truncation, etc. Stability-indicating methods include, but is not limited to, High Performance Liquid Chromatography (HPLC), size-exclusion HPLC (SEC), with or without denaturants such as SDS, guanidium HCl, or organic solvent in the sample or in mobile phase), reverse-phase (RP) HPLC, ion-exchange HPLC, electrophoresis, hydrophobic interaction chromatography (HIC), affinity chromatography, SDS-PAGE, disulfide reduction with reducing agent(s), native gel electrophoresis, capillary electrophoresis, analytical ultracentrifuge, light scattering, turbidity assay and protein concentration assay. Structure-stability studies can be performed by circular dichroism, fluorescence (intrinsic and hydrophobic probe binding), UV, FTIR, and/or differential scanning calorimetry. Thus, the effect of a particular excipient on monomeric protein aggregation or oligomerization can be determined for example by the change in soluble monomeric protein in solution over time.

In size exclusion HPLC or SEC, also known as gel filtration chromatography or molecular sieving chromatography, columns are designed with a porous matrix that retains molecules smaller than the pore size while larger molecules are excluded and eluate earlier. An isocratic gradient is used for most applications.

The present invention will now be described by its different aspects.

In a first aspect, the invention provides a method of preparing a stabilized bulk solution of a monomeric protein, the method comprising the steps of:
a) providing of a bulk of monomeric protein in a buffer solution, and
b) adding an excipient to the bulk, wherein the excipient is selected from the group consisting of:
  i) a bacteriostatic agent,
  ii) a surfactant,
  iii) an isotonicity agent,
  iv) an amino acid,
  v) an antioxidant,
  vi) an isotonicity agent and an antioxidant,
  vii) an isotonicity agent, an antioxidant and an amino acid,
  viii) an amino acid and an antioxidant,
  ix) an amino acid, an antioxidant and a surfactant,
  x) a bacteriostatic agent and an antioxidant, and
  xi) a bacteriostatic agent, an antioxidant and a surfactant.

The excipient(s) or combinations thereof can be further added at final formulation (FDF), and not only to a bulk of monomeric protein. In other words, the excipients can be added at various stages of a bulk of monomeric protein and also at final formulation steps of the manufacturing process, but at least once to the bulk of monomeric protein. Preferably, the monomeric protein is an interferon. More preferably, the interferon is IFN-beta. Even more preferably, the IFN-beta is human recombinant IFN-beta.

Preferably, the protein is stabilized against aggregation or oligomerization.

Preferably, the bacteriostatic agent is benzylalcohol, the surfactant is TWEEN 20, the isotonicity agent is mannitol, the amino acid is selected from the group consisting of lysine or arginine and the antioxidant is methionine. Preferred combinations of the excipients are:
1. the isotonicity agent is mannitol and the antioxidant is methionine,
2. the isotonicity agent is mannitol, the antioxidant is methionine and the amino acid is lysine,
3. the amino acid is lysine and the antioxidant methionine,
4. the amino acid is lysine, the antioxidant methionine and the surfactant is TWEEN 20,
5. the bacteriostatic agent is benzylalcohol and the antioxidant is methionine, or
6. the bacteriostatic agent is benzylalcohol, the antioxidant is methionine and the surfactant is TWEEN 20.

In addition, the bulk protein can be incubated at specific temperatures as to favor thermal dissociation of the bulk monomeric protein. Preferably, the temperature range is 27° C. to 31° C. Most preferably, the temperature is set to 29° C. Alternatively, the temperature is let for gradual increase, until reaching the specific temperatures mentioned above. Preferably, the incubation is performed during at least 3 hours or during a range of 6 hours to 40 hours. More preferably, the incubation is performed during a range of 15 hours to 30 hours or during 10 hours, 16 hours, 18.5 hours or 24 hours. Even more preferably, the incubation is performed during 24 hours. The incubation can be carried out before or after the preformulation step according to the first aspect of the invention, but not limited to. A monomeric protein that has been stabilized according to the first aspect of the invention can be incubated at any stage of the manufacturing process, i.e. also at final formulations steps.

In a second aspect, the invention provides a pre-formulated bulk protein obtained by the method according to the first aspect of the invention.

In a third aspect the invention provides a method for increasing and/or maintaining stability of a monomeric protein comprising the method of pre-formulation of the bulk of the protein according to the first aspect of the invention.

The invention will now be described by its preferred embodiment in light of a specific monomeric protein, interferon, and more preferably IFN-beta.

An "interferon" or "IFN", as used herein, is intended to include any molecule defined as such in the literature, comprising for example any types of IFNs mentioned in the above section "Background of the Invention". In particular, IFN-α, IFN-β and IFN-γ are included in the above definition. IFN-β is the preferred IFN according to the present invention. IFN-β suitable in accordance with the present invention is commercially available e.g. as REBIF (Serono), AVONEX (Biogen) or BETAFERON (Schering). The use of interferons of human origin is also preferred in accordance with the present invention. The term interferon, as used herein, is intended to encompass salts, functional derivatives, variants, analogs and active fragments thereof.

The term "interferon-beta (IFN-beta or IFN-β)", as used herein, is intended to include fibroblast interferon in particular of human origin, as obtained by isolation from biological fluids or as obtained by DNA recombinant techniques from prokaryotic or eukaryotic host cells, as well as its salts, functional derivatives, variants, analogs and active fragments. Preferably IFN-beta is intended to mean Interferon beta-1a.

As used herein the term "muteins" refers to analogs of IFN in which one or more of the amino acid residues of a natural IFN are replaced by different amino acid residues, or are deleted, or one or more amino acid residues are added to the natural sequence of IFN, without changing considerably the activity of the resulting products as compared to the wild type IFN. These muteins are prepared by known synthesis and/or by site-directed mutagenesis techniques, or any other known technique suitable therefore. Preferred muteins include e.g. the ones described by Shepard et al. (1981) or Mark et al. (1984).

Any such mutein preferably has a sequence of amino acids sufficiently duplicative of that of IFN, such as to have substantially similar or even better activity to an IFN. The biological function of interferon is well known to the person skilled in the art, and biological standards are established and available e.g. from the National Institute for Biological Standards and Control (http://immunology.org/links/NIBSC).

Bioassays for the determination of IFN activity have been described. An IFN assay may for example be carried out as described by Rubinstein et al., 1981. Thus, it can be determined whether any given mutein has substantially a similar, or even a better, activity than IFN by means of routine experimentation.

Muteins of IFN, which can be used in accordance with the present invention, or nucleic acid coding therefore, include a finite set of substantially corresponding sequences as substitution peptides or polynucleotides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of polypeptides or proteins of the invention, may include synonymous amino acids within a group, which have sufficiently similar physicochemical properties that substitution between members of the group will preserve the biological function of the molecule. It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

Preferably, the synonymous amino acid groups are those defined in Table I. More preferably, the synonymous amino acid groups are those defined in Table II; and most preferably the synonymous amino acid groups are those defined in Table III.

TABLE I

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE II

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE III

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of IFN, for use in the present invention include any known method steps, such as presented in U.S. Pat. Nos. 4,959,314, 4,588,585 and 4,737,462, to Mark et al; 5,116,943 to Koths et al., 4,965,195 to Namen et al; 4,879,111 to Chong et al; and 5,017,691 to Lee et al; and lysine substituted proteins presented in U.S. Pat. No. 4,904,584 (Shaw et al). Specific muteins of IFN-beta have been described, for example by Mark et al., 1984.

The term "fused protein" refers to a polypeptide comprising an IFN, or a mutein thereof, fused to another protein, which e.g., has an extended residence time in body fluids. An IFN may thus be fused to another protein, polypeptide or the like, e.g., an immunoglobulin or a fragment thereof.

"Functional derivatives" as used herein cover derivatives of IFN, and their muteins and fused proteins, which may be prepared from the functional groups which occur as side chains on the residues or the N- or C-terminal groups, by means known in the art, and are included in the invention as long as they remain pharmaceutically acceptable, i.e. they do not destroy the activity of the protein which is substantially similar to the activity IFN, and do not confer toxic properties on compositions containing it. These derivatives may, for example, include polyethylene glycol side-chains, which may mask antigenic sites and extend the residence of IFN in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

As "active fractions" of IFN, or muteins and fused proteins, the present invention covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has no significantly reduced activity as compared to the corresponding IFN.

The term "salts" herein refers to both salts of carboxyl groups and to acid addition salts of amino groups of the proteins described above or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of the proteins (IFN) relevant to the present invention, i.e., the ability to bind to the corresponding receptor and initiate receptor signaling.

In accordance with the present invention, the use of recombinant human IFN-beta and the compounds of the invention is further particularly preferred.

A special kind of interferon variant has been described recently. The so-called "consensus interferons" are non-naturally occurring variants of IFN (U.S. Pat. No. 6,013,253). According to a preferred embodiment of the invention, the compounds of the invention are used in combination with a consensus interferon.

As used herein, human interferon consensus (IFN-con) shall mean a non-naturally-occurring polypeptide, which predominantly includes those amino acid residues that are common to a subset of IFN-alpha's representative of the majority of the naturally-occurring human leukocyte interferon subtype sequences and which includes, at one or more of those positions where there is no amino acid common to all subtypes, an amino acid which predominantly occurs at that position and in no event includes any amino acid residue which is not existent in that position in at least one naturally-occurring subtype. IFN-con encompasses but is not limited to the amino acid sequences designated IFN-con1, IFN-con2 and IFN-con3 which are disclosed in U.S. Pat. Nos. 4,695,623, 4,897,471 and 5,541,293. DNA sequences encoding IFN-con may be produced as described in the above-mentioned patents, or by other standard methods.

In a further preferred embodiment, the fused protein comprises an Ig fusion. The fusion may be direct, or via a short linker peptide which can be as short as 1 to 3 amino acid residues in length or longer, for example, 13 amino acid residues in length. Said linker may be a tripeptide of the sequence E-F-M (Glu-Phe-Met), for example, or a 13-amino acid linker sequence comprising Glu-Phe-Gly-Ala-Gly-Leu-Val-Leu-Gly-Gly-Gln-Phe-Met introduced between the sequence of IFN and the immunoglobulin sequence. The resulting fusion protein may have improved properties, such as an extended residence time in body fluids (half-life), increased specific activity, increased expression level, or the purification of the fusion protein is facilitated.

In a further preferred embodiment, IFN is fused to the constant region of an Ig molecule. Preferably, it is fused to heavy chain regions, like the CH2 and CH3 domains of human IgG1, for example. Other isoforms of Ig molecules are also suitable for the generation of fusion proteins according to the present invention, such as isoforms $IgG_2$, $IgG_3$ or $IgG_4$, or other Ig classes, like IgM or IgA, for example. Fusion proteins may be monomeric or multimeric, hetero- or homomultimeric.

In a further preferred embodiment, the functional derivative comprises at least one moiety attached to one or more functional groups, which occur as one or more side chains on the amino acid residues. Preferably, the moiety is a polyethylene (PEG) moiety. PEGylation may be carried out by known methods, such as the ones described in WO99/55377, for example.

The present invention can generally be applied to all kind of interferon, to the ones mentioned above as well as including natural interferon, interferon produced by recombinant DNA technology, and interferon produced by chemical synthesis or modification. By interferon, it is also meant to encompass crude, semi-purified and purified interferon from fibroblasts, leukocytes, lymphocytes or any other interferon-containing or producing tissues from humans or any other appropriate species. Most preferably, the present invention is applicable to human fibroblast interferon (interferon-beta).

Preferably the concentration of IFN-beta in the preformulation is at or about 10 μg/ml to at or about 2000 μg/ml, more preferably at or about 100 μg/ml to at or about 1000 μg/ml, most preferably at or about 500 or at about 810 μg/ml.

Preferably, the buffer is present in an amount sufficient to maintain the pH of said composition within plus or minus 0.5 units of a specified pH, where the specified pH is about 3.5 to about 5.5. More preferably, the pH is 3.8, 4.2 or 4.7. Even more preferably, the pH is 4.7. Preferably, the buffer is present at a concentration at or about 5 mM to at or about 500 mM. Buffer concentrations in total solution can vary between at or about 5 mM, 9.5 mM, 10 mM, 50 mM, 100 mM, 150 mM, 200 mM, 250 mM, and 500 mM. Preferably the buffer concentration is at or about 10 mM or at or about 50 mM. Particularly preferred is a buffer at or about 50 mM in acetate ions with a pH of 4.7. Preferably, the buffer is acetate buffer with preferred counterions being sodium or potassium ions. Acetate saline buffers are well known in the art.

Preferably, the concentration of the isotonicity agent (for example mannitol) is present at or about 0.5 mg/ml to at or about 500 mg/ml. More preferably, the concentration of the isotonicity agent is at or about 55 mg/ml. Still more preferably, the concentration of the isotonicity agent is at or about 150 mM, or at or about 300 mM or at or about 600 mM.

Preferably, the concentration of the surfactant (i.e. TWEEN 20) is at or about 0.01 mg/ml to at or about 10 mg/ml. More preferably, the concentration of the surfactant is at or about 0.05 mg/ml.

Preferably, the concentration of the antioxidant (e.g. methionine) is present at or about 0.01 to at or about 5.0 mg/ml. More preferably, the concentration of the antioxidant is at or about 0.12 mg/ml or at or about 0.24 mg/ml.

Preferably, the amino acid is lysine or arginine. More preferably, the amino acid is lysine. Preferably, the concentration of the amino acid (e.g. lysine or arginine) is present at or about 20 to at or about 200 mg/ml. Preferably, the concentration of lysine is at or about 27 mg/ml or at or about 55 mg/ml or at or about 82 mg/ml or at or about 164 mg/ml. Preferably, the concentration of arginine is at or about 32 mg/ml or at or about 63 mg/ml.

Preferably, the concentration of the bacteriostatic agent (e.g. benzylalcohol) is at or about 0.01 mg/ml to at or about 200 mg/ml. More preferably, the concentration of the bacteriostatic agent is at or about 5 mg/ml or at or about 10 mg/ml.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning of a range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

EXAMPLES

The analytical methods used in the following examples are described in example 6.

Example 1

The Effect of Incubation Temperature and Incubation Time on Bulk-Interferon Stabilization (Thermal Dissociation)

The following experiments were performed in order to evaluate the effect of thawing temperature, incubation temperature and incubation time (duration) on the stabilization of a bulk interferon-beta. The objective was to reduce effectively and consistently the formation of interferon oligomers and/or interferon aggregates during manufacturing process. The following experiments apply primarily to frozen storage bulk interferon preparations (preparations stored below 0° C., e.g. at −20° C. or −70° C.) that are to be primarily thawed and then eventually incubated or stored at a given temperature and during a given time for further manufacturing processing. Considerations derived from these experiments could also be applied for preparations that are stored above 0° C. (e.g. 2-8° C.) and which are thus not subject to a thawing step (or temperature shifts) but that may suffer other kind of stresses. Herein, the term "resting" refers to a frozen preparation that is thawed (e.g. in an incubator, a bath or other location) and then stored (e.g. in an incubator, a bath or other location) at a given temperature during a given time; the term "resting temperature" refers to both the thawing temperature and the incubation temperature; if the frozen preparation is directly placed in an incubator, the terms "incubation temperature" or "resting temperature" can be used interchangeably; the term "resting time" refers to the total of thawing duration and storage duration (e.g. incubation duration) at a specific temperature; if the frozen preparation is directly placed in an incubator, the terms "incubation time" or "resting time" can be used interchangeably.

1.a Thermal Dissociation Small Lab Scale Experiment at Various Temperatures

In a first experiment, the effects of thawing temperature at either room temperature (RT), 25° C., 27° C. or 29° C., followed by incubation at either 25° C., 27° C. or 29° C. during a total of 16 hours or 24 hours were tested. The experiment is set up in a manner which doesn't interfere with the temperature settings, which are thus maintained stable during the whole procedure. Table 4 as well as FIG. 1 summarizes the procedure. Levels of interferon oligomers and interferon aggregates were measured by a new SEC-HPLC method, which is herein referred to as NEW SEC. The NEW SEC method is able to detect both non-covalent and covalent oligomers both quantitatively and qualitatively.

The objective was to optimize the thermal dissociation (TD) of Bulk interferon, in order to reduce oligomerization and/or aggregation to minimum before drug product preparation (damage repair) by the following parameters or variables:

1) Effect of incubation temperature (25° C., 27° C. and 29° C.) on the thermal dissociation efficiency,
2) Effect of the incubation duration on the thermal dissociation efficiency,
3) Shortening the thawing duration by thawing in an incubator.

TABLE 4

| EXP. | Set 1 | | | Set 2 | | | Control |
|---|---|---|---|---|---|---|---|
| Thawing Temp ° C. | RT | RT | RT | 25 | 27 | 29 | RT |
| *Incubation Temp. ° C. | 25 | 27 | 29 | 25 | 27 | 29 | RT |

*Total Thawing and Incubation time is either 16 hours or 24 hours

Control at RT was performed one time, EXP Set 1 was performed two times and EXP Set 2 was performed three times. For each condition, one 250 ml tube equipped with a small scale model (2 ml nunc tube filled with 1.8 ml "fresh" bulk interferon, the "inserted tube model") was used. The incubator is either water jacketed or one with air circulation.

Glossary/Abbreviations

| | |
|---|---|
| Agg | Aggregates |
| COA | Certificate of analysis. |
| Dim | Dimers |
| Deg | Degradants |
| FDF | Final dosage form |
| F/T | Freezing and thawing |
| r-h IFN-beta 1a | Recombinant human interferon-beta 1a (r-h IFN-beta 1a) from CHO cells. |
| r-h IFN-beta FDF | r-h IFN-beta 1a final dosage form (r-h IFN-beta FDF) |
| SE-HPLC | Size exclusion high performance liquid chromatography |
| SAB | 50 mM sodium acetate pH-3.8 |
| Temp. | Temperature |

1. Equipments and Materials of the New SEC-HPLC method:
   HPLC system: Waters Alliance
   UV detector: Waters 996 PDA wavelength 214 nm
   Autosampler temperature setting: 4° C.
   Column TosoHaas TSK G2000 $SW_{XL}$
   Column temperature: room temperature
   Mobile phase: 50 mM Sodium acetate pH 3.8 with 50 mM NaCl Prepared by dissolving 5.84 gr NaCl in 2 liter 50 mM Sodium acetate pH 3.8 buffer. The acetate buffer was prepared at sterile solution unit by adding acetic acid to WFI and titrating with a solution of 10M NaOH up to pH-3.8.

Flow rate: 0.5 mL/min

Inj Volume: 200 µL r-h IFN-beta 1a bulk 0.34-0.36 mg/mL.

Reagents:

Acetic, Merck code K31358056

NaOH, Merck B197582

NaOH 10M solution

WFI

NaCl, JT BAKER code 3627-07

2. Procedure—the Procedure is Illustrated in FIG. 1:

1) 1.8 ml of fresh r-h IFN-beta 1a Bulk was inserted in 2 ml nunc tubes and frozen at −70° C. inside 250 ml tubes containing 200 ml water.

2) Three tubes were thawed at RT and incubated separately at 25° C., 27° C. and 29° C. in validated incubators (stable of fixed temperatures over time) for a total of 16 hours. The tubes were sampled for testing by NEW SEC after thawing and after 16 hours (thawing+incubation).

3) Three tubes were thawed at RT and incubated separately at 25° C., 27° C. and 29° C. in validated incubators for a total of 24 hours. The tubes were sampled for testing by NEW SEC after thawing and after 24 hours (thawing+incubation)

4) Three tubes were thawed and incubated separately at 25° C., 27° C. and 29° C. in validated incubators for a total of 16 hours. The tubes were sampled for testing by NEW SEC after thawing and after 16 hours (thawing+incubation).

5) Three tubes were thawed and incubated separately at 25° C., 27° C. and 29° C. in validated incubators for a total of 16 hours. The tubes were sampled for testing by NEW SEC after 16 hours (thawing+incubation)—sampling after thawing in the incubator was not done.

6) Three tubes were thawed and incubated separately at 25° C., 27° C. and 29° C. in incubators for a total of 24 hours. The tubes were sampled for testing by NEW SEC after 24 hours (thawing+incubation)-sampling after thawing in the incubator was not done.

7) A tube was thawed at RT for 16 hours and stored at 2-8° C. for up to 72 hours—the tube was sampled for NEW-SEC to serve as control for this experiment.

8) In order to evaluate effect on the molecule, the experiment was repeated on the chosen conditions. Incubated Samples were tested by NEW SEC, IEF, QUANT-HPLC, ES-MS, BIOASSAY, DEG/OX HPLC, CZE. Results were compared to a control sample thawed at RT for 16 hours and stored at 2-8° C.

3. Results: % Mon or % Monomer=% of r-h IFN-beta 1a monomers

% Agg=% of r-h IFN-beta 1a aggregates

Thawing at RT and Incubating for a Total of 16 hours

3×250 ml tubes with inserts were frozen at −70° C. and thawed at RT, the tubes were gently inverted twenty times, sampled and immediately transferred into three incubators (25° C., 27° C. and 29° C.) for a total of 16 hours (thawing+Incubation). Samples were stored at 2-8° C. until analysis by NEW SEC-HPLC. Results are shown in table 5.

TABLE 5

| Condition** | % Monomer | % Agg | % Dimer | Thawing Duration |
|---|---|---|---|---|
| 25° C. | 88.05 | 0.64 | 11.3 | 6 hours |
| 27° C. | 92.58 | 0.70 | 6.7 | 21-22.3° C. |
| 29° C. | 95.7 | 0.56 | 3.7 | |

**Incubation duration-10 hours

Thawing at RT and Incubating for a Total of 24 hours

3×250 ml tubes with inserts were frozen at −70° C. and thawed at RT, the tubes were gently inverted twenty times, sampled and immediately transferred into three incubators (25° C., 27° C. and 29° C.) for a total of 24 hours (thawing+Incubation). Samples were stored at 2-8° C. until analysis by NEW SEC-HPLC. Results are shown in table 6.

TABLE 6

| Condition** | % Mon | % Agg | % Dimer | Thawing Duration |
|---|---|---|---|---|
| 25° C. | 92.25 | 0.58 | 7.1 | 5 hours and |
| 27° C. | 96.4 | 0.5 | 3.1 | 30 min |
| 29° C. | 97.31 | 0.44 | 2.2 | 21.6-22.2° C. |

**Incubation duration-18.5 hours

Thawing in an Incubator and Incubating for a Total of 16 hours 3×250 ml tubes with inserts were frozen at −70° C. and thawed separately inside three incubators (25° C., 27° C. and 29° C.), the tubes were gently inverted twenty times after thawing and incubated for a total of 16 hours (thawing+Incubation). Samples were stored at 2-8° C. until analysis by NEW SEC-HPLC. Results are shown in table 7.

| Condition** | % Monomer | % Agg | % Dimer | Thawing Duration |
|---|---|---|---|---|
| 25° C. Air Circulation | 90.22 | 0.52 | 9.2 | 3 hours and 9 min |
| 27° C. Water Jacketed | 93.53 | 0.56 | 5.9 | 5 hours |
| 29° C. Water Jacketed | 95.95 | 0.47 | 3.6 | 3 hours and 32 min |

**Incubation duration-16 hours

Thawing in a Incubator and Incubating for a Total of 24 hours 3×250 ml tubes with inserts were frozen at −70° C. and thawed separately inside three incubators (25° C., 27° C. and 29° C.), the tubes were gently inverted twenty times, sampled for NEW SEC HPLC and incubated for a total of 24 hours (thawing+Incubation). Samples were stored at 2-8° C. until analysis by NEW SEC-HPLC. The experiment was repeated on a separate day—without sampling the tubes after thawing. Results are shown in table 8a and 8b.

TABLE 8a

| Condition** | % Monomer | % Agg | % Dimer | Thawing Duration |
|---|---|---|---|---|
| Immediately after thawing at 25° C. | 77.48 | 1.63 | 20.89 | 3 hours and 21 min |

TABLE 8a-continued

| Condition** | % Monomer | % Agg | % Dimer | Thawing Duration |
|---|---|---|---|---|
| Immediately after thawing at 27° C. | 77.2 | 1.73 | 21.07 | 5 hours |
| Immediately after thawing at 29° C. | 78.56 | 1.64 | 19.8 | 3 hours 30 |
| Immediately after thawing at RT | 77.42 | 1.65 | 20.92 | 6 hours |

**Incubation duration-24 hours

| Condition | % Monomer | % Agg | % Dimer | Thawing Duration |
|---|---|---|---|---|
| 25° C.-A | 93.42 | 0.42 | 6.1 | 3 hours |
| 25° C.-B | 93.15 | 0.51 | 6.3 | and 8 min |
| 27° C.-A | 96.32 | 0.54 | 3.1 | 5 hours |
| 27° C.-B | 96.22 | 0.57 | 3.2 | |
| 29° C.-A | 97.85 | 0.53 | 1.6 | 3 hours |
| 29° C.-B | 97.58 | 0.51 | 1.9 | and 30 min |

4. Conclusion:

The following points can be set forth from the above experiments:

Increasing the incubation temperature and duration increases the thermal dissociation efficiency.

Thawing duration is decreased when thawing inside an incubator compared to thawing at RT and therefore increases monomer level.

Thawing and Incubation at 25° C., 27° C. and 29° C. for up to 24 hours had no negative effect on the r-h IFN-beta 1a molecule according to: Routine SEC HPLC, Deg/Ox HPLC, quant-HPLC, ES-MS, Bioassay and CZE.

The above experiments demonstrate that significant results are obtained in terms of lowering oligomerization by adjusting the resting temperature and resting time of a previously frozen stored bulk interferon.

Independently on how the preparation is defrozen (e.g. thawed at RT or thawed in an incubator), increasing resting temperature up to a certain point has a beneficial outcome on interferon monomer level. Thus, there is a correlation between resting temperature and protein monomer level; rising resting temperature from 25° C. to 29° C. leads to an increase in protein monomer level. The best results are obtained when the bulk solution is set at a temperature of 29° C. Preferably, the bulk solution is placed in an incubator at an incubation temperature of 29° C. Comparing the incubation temperatures, an increase of ~5-6% monomers is observed from 25° C. to 29° C. Preferably, the frozen preparation is directly placed in an incubator and not thawed at RT before incubation (thus thawing occurs in the incubator). Results also show that incubating a defrozen bulk interferon during 10 hours already yields a percentage of monomers higher than 95%. If defrozen at RT, incubation durations tested were either 10 or 18.5 hours. If defrozen in an incubator, incubation durations tested were either 16 or 24 hours.

Likewise, resting time is also a factor that influences oligomerization. Independently of the resting conditions (e.g. thawed at RT and then incubated or directly incubated), there's a correlation between resting time and monomer level; longer resting times increase protein monomer level. The best results are obtained at a resting time of 24 hours. Comparing resting times, a gain of ~3% monomers is achieved from a resting time of 16 hours to 24 hours. Preferably, the resting time for the frozen preparation is 24 hours. More preferably, the frozen preparation is directly placed in an incubator (thawing occurs in the incubator) for an incubation time (resting time) of 24 hours.

Combining the two variables (resting time and resting temperature), an increase of ~9% monomers can thus be achieved. The results are even more striking when comparing incubated formulations with those that aren't. A 77.48% Mon is obtained if the preparation is analyzed directly after thawing (not incubated), whereas 97.9% Mon is obtained when the frozen preparation is directly incubated for an incubation time of 24 hours at an incubation temperature of 29° C. Thus, a 20% difference in monomer level is obtained by optimizing the two variables. Preferably, the bulk interferon is set at a resting temperature of 29° C. during a resting time of 24 hours. More preferably, the bulk interferon is directly incubated at 29° C. (thawing occurs in the incubator) for an incubation time of 24 hours (best results yield 97.9% Mon).

In conclusion, resting time and resting temperatures and preferably incubation temperature and incubation time are important factors that contribute significantly to maintaining and/or increasing stabilization of a bulk interferon preformulation or formulation.

1.b Lab Scale Thermal Dissociation Experiments at 29° C. with various F/T cycles This report evaluates the effect of incubation at 29° C. on the level of dimers and aggregates in r-h IFN-beta 1a drug substance.

1. Procedure:
   a. The NEW-SEC method was used for analyzing r-h IFN-beta 1a bulk samples that were incubated at 29° C. for 15 hours or 3 hours after thawing and which were subject to various F/T cycles as indicated in table 9. R-h IFN-beta 1a Bulk was transferred into seven 15 ml corning tubes (0.9 ml in each tube). The tubes were frozen at −70° C. IFN-β-1a Bulk (previously frozen and thawed) was also transferred into two 250 ml corning tubes (200 ml in each tube), the tubes were frozen at −70° C.

TABLE 9

Sample treatment for thermal dissociation experiment at lab scale

| Sample | F/T Cycles | Thawing | Storage before analysis by SEC-HPLC |
|---|---|---|---|
| 1 | 1 | Room Temp-2 hours | Stored at 4° C. |
| 2 | 1 | Room Temp-2 hours | 29° C. in a dry incubator for 15 hours |
| 3 | 1 | In a water circulating bath at 29° C. for 4 min | 29° C. in a dry incubator for 15 hours |
| 4 | 4 | Room Temp-2 hours | Stored at 4° C. |
| 5 | 4 | Room Temp-2 hours | 29° C. in a dry incubator for 15 hours |
| 6 | 4 | Room Temp-2 hours | 29° C. in a dry incubator for 3 hours |
| 7 | 4 | In a water circulating bath at 29° C. for 4 min | 29° C. in a dry incubator for 15 hours |
| 8 (250 ml tube) | 2 | Room Temp-7 hours | 29° C. in a dry incubator for 15 hours |
| 9 (250 ml tube) | 2 | Room Temp-7 hours | Stored at 4° C. | b. In order to evaluate the effect of incubating IFN-β-1a bulk on the molecule, the incubated bulk (after 1 F/T) was tested by the following methods: Deg/Ox-HPLC, IEF, ES-MS, Quant-HPLC, CZE.

c. In addition, kinetics of thermal dissociation at labscale F/TX1 was also performed. Aliquots from r-h IFN-beta 1a bulk in 250 ml tube, after F/TX1 were dispensed in 15 ml tube and incubated at 29° C. in an incubator.

2. Results:
1) Incubation of r-h IFN-beta 1a bulk (1 F/T) after thawing at room temp. increased the monomer level from 82.8% to 97.57% and decreased the aggregate level from 0.7% to 0.2% (see Table 10). Incubation at 29 C (incubator) for 15 hr is effective for dimer dissociation. 2) Incubation of r-h IFN-beta 1a bulk after thawing in a bath increased the monomer level from 82.8% to 96.7% but increased the aggregate level from 0.7% to 1.97% (see Table 10).

TABLE 10

SEC-HPLC Results of 0.9 ml Bulk Samples After 1 F/T

| Sample name | AGGR % AREA | DIMERS % AREA | MONOMERS % AREA |
|---|---|---|---|
| F/TX1 Thawed at RT 2 hr, | 0.72 | 17.01 | 82.27 |
| Stored-4° C. - Control | 0.69 | 15.88 | 83.43 |
| AVG | 0.70 | 16.4 | 82.85 |
| F/TX1 Thawed at RT 2 hr, | 0.23 | 2.3 | 97.47 |
| Incubated at 29° C. - 15 hours | 0.19 | 2.14 | 97.67 |
| AVG | 0.21 | 2.22 | 97.57 |
| F/TX1 Thawed in a bath (29° C., 4 min.), | 1.97 | 1.43 | 96.6 |
| Incubated at 29° C. - 15 hours | 1.97 | 1.18 | 96.85 |
| AVG | 1.97 | 1.30 | 96.72 |

3) Incubation of r-h IFN-beta 1a bulk (4 FT) for 3 hours after thawing at room temp. increased the monomer level from 82.3% to 89.5% due to the decrease in dimer level (see table 11 and FIG. 2).
4) Incubation of r-h IFN-beta 1a bulk for 15 hours (4 FT) after thawing at room temp. further increased the monomer level (compared to 3 hours incubation) from 82.3% to 93.7.% due to the decrease in dimer level (see table 11 and FIG. 2).
5) Incubation of r-h IFN-beta 1a bulk after thawing in a bath increased the monomer level from 82.3% to 94.7% due to the decrease in dimer level (see table 11 and FIG. 2).

TABLE 11

SEC-HPLC Results of 0.9 ml Bulk Samples After 4 f/T

| Sample name | AGGR % AREA | DIMERS % AREA | MONOMERS % AREA |
|---|---|---|---|
| F/TX4 Thawed at RT | 2.89 | 14.16 | 82.95 |
| 2 hr, Stored-4° C. - Control | 3.03 | 15.26 | 81.71 |
| AVG | 2.96 | 14.71 | 82.33 |
| F/TX4 Thawed at RT | 2.98 | 7.66 | 89.36 |
| 2 hr, Incubated at 29° C. - 3 hours | 2.92 | 7.42 | 89.66 |
| AVG | 2.95 | 7.54 | 89.51 |
| F/TX4 Thawed at RT | 2.97 | 3.45 | 93.58 |
| 2 hr, Incubated at 29° C. - 15 hours | 2.91 | 3.27 | 93.82 |
| AVG | 2.94 | 3.36 | 93.7 |
| F/TX4 Thawed In a bath, | 2.89 | 2.38 | 94.73 |
| Incubated at 29° C. - 15 hours | 2.83 | 2.31 | 94.86 |
| AVG | 2.86 | 2.34 | 94.79 |

6) Incubation of a 200 ml r-h IFN-beta 1a bulk sample after thawing at room temp. increased the momomer level from 73% to 91.2% and decreased the agg level from 3.9% to 2.9% (see table 12 and FIG. 3).

TABLE 12

SEC-HPLC Results Of 200 ml Bulk Samples After 2 F/T

| Sample name | AGGR % AREA | DIMERS % AREA | MONOMERS % AREA |
|---|---|---|---|
| 200 ml thawed at RT 7 hr, | 4.06 | 23.3 | 72.64 |
| stored at 4° C. control | 3.85 | 22.71 | 73.44 |
| AVG | 3.9 | 23.0 | 73.04 |
| 200 ml thawed at RT 7 hr, | 2.98 | 5.65 | 91.37 |
| Incubated at 29° C. 15 hours | 2.95 | 6.05 | 91 |
| AVG | 2.9 | 5.8 | 91.18 |

7) The incubated r-h IFN-beta 1a bulk samples (0.9 ml, 1 F/T) were analyzed by the following tests together with the control sample thawed at R.T and stored at 4° C. (see table 13):

Deg/Ox-HPLC—no increase in the level of oxidation was seen in incubated samples compared to the control sample (stored at 4° C.)

ES-MS—no difference in the carbohydrate level was seen in incubated samples compared to the control sample Quant-HPLC—no significant differences in concentration was seen CZE—Identical electropherogram profiles were obtained IEF—The r-h IFN-beta 1a F bulk sample that was thawed in a circulating water bath showed an additional band around pI −7. The control sample and the sample thawed at R.T and incubated for 15 hours conformed to specifications.

TABLE 13

EFFECT OF THERMAL DISSOCIATION ON THE IFN

| Sample | Deg-Ox % | ES-MS NON | MONO | DI | TRI | IEF 8.9-9 | 8.5 | 7.9-8.0 | Q HPLC ug/ml | CZE |
|---|---|---|---|---|---|---|---|---|---|---|
| F/TX1 Thaw. RT, 4 C. | 99.3 | 1 | 15 | 72 | 12 | 19 | 58 | 23 | 334 | conf. |
| F/TX1 Thaw. RT, 29 C. 15 hr | 99.4 | 1 | 15 | 71 | 12 | 20 | 55 | 24 | 338 | conf. |
| F/TX1 Thaw. 29c, 29 C., 15 hr | 99.4 | 2 | 16 | 70 | 12 | 15 | 56 | 28 | 363 | conf. |

15 hours following thawing in room temperature do not affect the parameters of the IFN-β-1a molecule as determined by Deg/ox HPLC, ES-MS, Quant-HPLC CZE and IEF.

8) Results of kinetics of thermal dissociation at F/TX1 are shown in table 14 and in FIGS. 4 to 6.

TABLE 14

Kinetics of thermal dissociation at labscale F/TX1.

| Time hr. | Monomer | Dimer | Aggregate |
|---|---|---|---|
| 0 | 73.4 | 24.7 | 1.94 |
| 3 | 90.04 | 8.54 | 1.42 |
| 6 | 94.13 | 4.7 | 1.19 |
| 9 | 95.09 | 3.79 | 1.12 |
| 12 | 95.92 | 3.09 | 0.99 |
| 15 | 96.56 | 2.54 | 0.91 |
| 24 | 97.2 | 1.94 | 0.87 |

3. Conclusions:
1) Incubating r-h IFN-beta 1a samples at 29° C. for 15 hours after thawing at room temp. significantly decreased the level of oligomerization (mainly dimers)
2) Incubating r-h IFN-beta 1a samples at 29° C. for 15 hours after thawing at 29° C. in a bath significantly decreased the level of oligomerization.
3) Based on the analytical methods used, incubation of the r-h IFN-beta 1a for 15 hours at 29° C. bulk after thawing at RT did not have a negative effect on the parameters of the IFN-β-1a molecule as determined by Deg/ox HPLC, ES-MS, Quant-HPLC CZE and IEF. Effective in dissociating non covalent oligomers, but not all non covalent oligomers are dissociated (4% non covalent oligomers not dissociated in the 250 ml tubes) % Monomers in 250 ml tubes reached 94% (9 hr incubation 29 C) and 97.57% in small tubes (15 hr incubation 29 C). Equilibrium of oligomers reached immediately after thermal dissociation (see tables and figures). Thermal dissociation at 29° C. in 15 ml tubes is completed after 15 hours. In summary, the present experiments (1.a and 1.b) demonstrate that thermal dissociation, embodied by a specific temperature and duration (i.e. resting temperature and resting time or incubation time and incubation temperature), is crucial for maintaining and/or increasing stability of a (monomeric) protein or formulation containing the (monomeric) protein. Kinetics of thermal dissociation for interferon-beta further shows that thermal dissociation at 1 F/T cycle yields a 90% Mon after only 3 hours, is almost completed after 6 hours, and reaches then a "plateau" at 15 hours. Preferably, thermal dissociation is performed during at least 3 hours. More preferably, the duration (resting time or incubation time) of thermal dissociation for interferon-beta is set in a range of 6 hours to 40 hours. Even more preferably, the duration of thermal dissociation for interferon-beta is set in a range of 15 hours to 30 hours, or during 10 hours, 16 hours, 18.5 hours or 24 hours. Still even more preferably, the duration of thermal dissociation for interferon-beta is 24 hours. The incubation or resting temperature is preferably set in a range of 27° C. to 31° C. More preferably, the temperature is 29° C. Even though the results for kinetics of thermal dissociation have been performed after 1 F/T, the man of art, using conventional techniques, could easily determine the kinetics of thermal dissociation after many F/T cycles (e.g. 2 F/T, 4 F/T or 11 F/T; or after any other kind of stress) or even for the entire manufacturing process or any part thereof of any interferon-beta (e.g. r-h interferon-beta 1a) or of any monomeric protein. As such, the present invention should not be limited to a particular incubation time or duration (or resting time). Likewise, the man of art, using conventional techniques, could easily determine the most appropriate incubation temperature (or resting temperature) after one or more F/T cycles (or after any other kind of stress) or even for the entire manufacturing process or any part thereof of any interferon-beta (e.g. r-h interferon-beta 1a) or of any monomeric protein. As such, the present invention should not be limited to a particular incubation temperature (or resting temperature).

Example 2

Stabilization of Interferon-Beta by the Addition of an Excipient to the Bulk-Interferon These experiments were conducted to verify the protective effect shown by some excipients like amino acids, bacteriostatic agents, surfactants and isotonicity agents on a bulk r-h IFN-beta 1a in terms of oligomerization and aggregation. The following studies were conducted without the addition of human serum albumin (HSA) to the bulk r-h IFN-beta 1a preformulations.

1.0 Glossary/Abbreviations

| | |
|---|---|
| Agg | Aggregates |
| COA | Certificate of analysis. |
| Dim | Dimers |
| Deg | Degradants |
| FDF | Final dosage form |
| F/T | Freezing and thawing |
| r-h IFN-beta 1a | Recombinant human interferon-beta 1a (r-h IFN-beta 1a) from CHO cells. |
| r-h IFN-beta FDF | r-h IFN-beta 1a final dosage form (r-h IFN-beta FDF) |
| SE-HPLC | Size exclusion high performance liquid chromatography |
| SAB | 50 mM sodium acetate pH-3.8 |
| Temp. | Temperature |

2.0 Introduction

The study focused on minimization of oligomerization of r-h IFN-beta 1a during manufacturing steps from the SEC-EL fraction to the FDF storage in order to provide a stabilized bulk interferon-beta.

Minimizing oligomerization generated by stresses (e.g. F/T) was performed by:
 1. Pre-formulating the bulk with excipients and/or other stabilizing agents and without HSA.
 2. Evaluating the effect of storage temperatures (−20° C., −70° C. & 2-8° C.) on oligomerization in preformulated bulk.

Preformulated bulk samples were analysed using SE-HPLC.

3.0 Purpose/Scope

To minimize the oligomerization of r-h IFN-beta 1a during bulk processing.

4.0 Equipment and Materials 4.1 Equipment 0.2μ filter unit P/N MPGL025 Millipore Millex syringe driven 0.2μ filter—P/N SLGV025LS Millipore 250 ml conical centrifuge tubes—Corning 1.8 ml cryotubes—Nunc 4.2 Materials
  a. SEC el2 fraction
  b. D-Mannitol DAB, Ph Eur, BP, USP, FCC, E421 (code 1.05980, Merck)
  c. Glacial acetic acid 100% (code 1.00063, Merck)
  d. Sodium hydroxide 10M
  e. Poloxamer 188 (Lutrol F 68 DAC, USP/NF, Basf, 5163315
  f. L-Methionine (1.05707, Merck)
  g. Benzyl alcohol Ph Eur, BP, NF (code 1.00987, Merck)
  h. L-Arginine monohydrochloride (code 1.01544, Merck)
  i. TWEEN 20 Ph Eur, NF (code 8.17072, Merck)
  j. Lysine (code 1.05701, Merck)
  k. r-h IFN-beta 1a 0.48-0.5 mg/ml or 0.088 mg/ml
  l. Acetate Buffer pH3.8 50 mM or 10 mM Stabilizers:
  Amino Acids:
    1. Arginine 31.6 mg/ml
    2. Lysine 27.4 mg/ml
    3. Methionine 0.12 mg/ml (Antioxidant)
  Surfactants:
    1. TWEEN 20 0.05 mg/ml
    2. Poloxamer 188 (Pluronic acid) 0.5 mg/ml
  Bacteriostatic Agent:
    1. Benzylalcohol 5 mg/ml
  Isotonicity Agent:
    1. Mannitol 54.6 mg/ml 5.0 Procedure The study was carried out on SEC-EL2 fractions.
The outline scheme of the study is shown in FIG. 7.
The different preformulation conditions are shown in tables 15 and 16.

TABLE 15

Experimental scheme

| Stabilizer | Surfactant | Antioxidant | 4 C. 2 ml tube | −20 C. 250 ml tube | −20 C. 2 ml tube | −70 C. 250 ml tube | −70 C. 2 ml tube |
|---|---|---|---|---|---|---|---|
| + | — | — | + | + | + | + | + |
| + | — | L-Methionine | + | — | + | — | + |
| + | Tween 20 | L-Methionine | + | — | + | — | + |
| + | Poloxamer 188 | L-Methionine | + | — | + | — | + |
| − | — | — | + | + | + | + | + |

Stabilizer: Benzyl alcohol/L-arginine/Mannitol/Lysine

TABLE 16

Preformulation conditions tested

| Cond. | Acetate pH | Benzyl alcohol mg/ml | L-Arg HCl mg/ml | Mannitol mg/ml | Lysine mg/ml | Poloxamer 188 mg/ml | Tween 20 mg/ml | L-Met mg/ml | No of Tubes |
|---|---|---|---|---|---|---|---|---|---|
| 1 | 50 mM pH-3.8 | 5 | — | — | — | — | — | — | 4 × 250 ml 6 × 2 ml |
| 2 | | 5 | — | — | — | — | — | 0.12 | 6 × 2 ml |
| 3 | | 5 | — | — | — | — | 0.05 | 0.12 | 6 × 2 ml |
| 4 | | 5 | — | — | — | 0.5 | — | 0.12 | 6 × 2 ml |
| 5 | | — | 31.6 | — | — | — | — | — | 4 × 250 ml 6 × 2 ml |
| 6 | | — | 31.6 | — | — | — | — | 0.12 | 6 × 2 ml |
| 7 | | — | 31.6 | — | — | — | 0.05 | 0.12 | 6 × 2 ml |
| 8 | | — | 31.6 | — | — | 0.5 | — | 0.12 | 6 × 2 ml |
| 9 | | — | — | 54.6 | — | — | — | — | 4 × 250 ml 6 × 2 ml |
| 10 | | — | — | 54.6 | — | — | — | 0.12 | 6 × 2 ml |
| 11 | | — | — | 54.6 | — | — | 0.05 | 0.12 | 6 × 2 ml |
| 12 | | — | — | 54.6 | — | 0.5 | — | 0.12 | 6 × 2 ml |
| 13 Control | | — | — | — | — | — | — | — | 2 × 250 ml 6 × 2 ml |
| 14 Control | 10 mM pH-3.8 | — | — | — | — | — | — | — | 6 × 2 ml |
| 15 | 50 mM pH-3.8 | — | — | — | 27.4 | — | — | — | 4 × 250 ml 6 × 2 ml |
| 16 | | — | — | — | 27.4 | — | — | 0.12 | 6 × 2 ml |
| 17 | | — | — | — | 27.4 | — | 0.05 | 0.12 | 6 × 2 ml |
| 18 | | — | — | — | 27.4 | 0.5 | — | 0.12 | 6 × 2 ml |

6.1 Preparation of Solutions

6.1.1 Preparation of 1 liter 50 mM sodium acetate pH-3.8 (SAB)

To 1000 ml WFI, 3.003 gr glacial acetic acid was added and mixed for 5 minutes.

Approximately 0.56 ml sodium hydroxide 10M was added in order to adjust to pH-3.8, the solution was mixed for 5 minutes, sampled for conductivity and filtered on a 0.2µ filter. Poloxamer 188 (or Pluronic F-68) is included in the preformulation at a level of 0.1% (Critical Micellar Concentration) in order to prevent adsorption of the drug substance by the surface of the containers during the manufacturing process; higher concentrations may negatively affect the stability of the product (higher oxidation); lower concentrations may be less effective in limiting adsorption.

6.1.2 One Liter of the Following Solutions were Prepared:

1. 50 mM acetate pH-3.8, 10 mg/ml Benzyl Alcohol
   As in 6.1.1 with the addition of 10 gr Benzyl alcohol before adding sodium hydroxide.
2. 50 mM acetate pH-3.8, 5 mg/ml Benzyl Alcohol
   As in 6.1.1 with the addition of 5 gr Benzyl alcohol before adding sodium hydroxide.
3. 50 mM acetate pH-3.8, 63.2 mg/ml Arginine
   As in 6.1.1 with the addition of 63.2 gr Arginine before adding sodium hydroxide.
4. 50 mM acetate pH-3.8, 31.6 mg/ml Arginine
   As in 6.1.1 with the addition of 31.6 gr Arginine before adding sodium hydroxide.
5. 50 mM acetate pH-3.8, 54.8 mg/ml Lysine
   As in 6.1.1 with the addition of 54.8. gr Lysine before adding sodium hydroxide.
6. 50 mM acetate pH-3.8, 27.4 mg/ml Lysine
   As in 6.1.1 with the addition of 27.4 mg/ml Lysine before adding sodium hydroxide.
7. 50 mM acetate pH-3.8, 600 mM mannitol
   To 0.926 kg WFI, 3.003 gr glacial acetic acid was added and the solution was mixed for 5 minutes. 100.3 gr mannitol was added to the solution and mixed for 5 minutes. Approximately 0.56 ml sodium hydroxide 10M was added in order to adjust to pH-3.8, the solution was mixed for 5 minutes, sampled for conductivity and filtered on a 0.2µ membrane.
8. 50 mM acetate pH-3.8, 300 mM mannitol
   To 0.966 kg WFI, 3.003 gr glacial acetic acid was added and mixed for 5 minutes. 55.1 gr mannitol was added and mixed for 5 minutes. Approximately 0.56 ml sodium hydroxide 10M was added in order to adjust to pH-3.8, the solution was mixed for 5 minutes, sampled for conductivity and filtered on a 0.2µ filter.

6.1.3 One Liter of the Following Solutions were Prepared:

1. 50 mM acetate pH-3.8, 5 mg/ml Benzyl Alcohol, 12 mg/ml Methionine
   As in 6.1.2 with the addition of 12 gr Methionine.
2. 50 mM acetate pH-3.8, 5 mg/ml Benzyl Alcohol, 12 mg/ml Methionine, 50 mg/ml Poloxamer 188
   As in 6.1.2 with the addition of 12 gr Methionine and 50 gr Poloxamer 188.
3. 50 mM acetate pH-3.8, 5 mg/ml Benzyl Alcohol, 12 mg/ml Methionine, 5 mg/ml TWEEN 20
   As in 6.1.2 with the addition of 12 gr methionine and 5 gr TWEEN 20
4. 50 mM acetate pH-3.8, 31.6 mg/ml Arginine, 12 mg/ml Methionine
   As in 6.1.2 with the addition of 12 gr Methionine
5. 50 mM acetate pH-3.8, 31.6 mg/ml Arginine, 12 mg/ml Methionine, 50 mg/ml Poloxamer 188
   As in 6.1.2 with the addition of 12 gr methionine and 50 gr Poloxamer 188.
6. 50 mM acetate p-3.8, 31.6 mg/ml Arginine, 12 mg/ml Methionine, 5 mg/ml TWEEN 20
   As in 6.1.2 with the addition of 12 gr Methionine and 5 gr TWEEN 20
7. 50 mM acetate pH-3.8, 300 mM Mannitol. 12 mg/ml Methionine
   As in 6.1.2 with the addition of 12 gr Methionine.
8. 50 mM acetate pH-3.8, 300 mM Mannitol, 12 mg/ml Methionine, 5 mg/ml Poloxamer 188
   As in 6.1.2 with the addition of 12 gr Methionine and 5 gr Poloxamer 188.
9. 50 mM acetate pH-3.8, 300 mM Mannitol, 12 mg/ml Methionine, 5 mg/ml TWEEN 20
   As in 6.1.2 with the addition of 12 gr Methionine and 5 gr TWEEN 20
10. 50 mM acetate pH-3.8, 27.4 nm/ml Lysine, 12 mg/ml Methionine
    As in 6.1.2 with the addition of 12 gr Methionine.
11. 50 mM acetate pH-3.8, 27.4 mg/ml Lysine, 12 mg/ml Methionine, 5 mg/ml Poloxamer 188
    As in 6.1.2 with the addition of 12 gr Methionine and 5 gr Poloxamer 188.
12. 50 mM acetate pH-3.8, 27.4 mg/ml Lysine, 12 mg/ml Methionine, 5 mg/ml TWEEN 20
    As in 6.1.2 with the addition of 12 gr Methionine and 5 gr TWEEN 20.

6.2 Bulk Preformulation

The outline scheme of the bulk preparation and composition is shown in FIG. 7 and Table 15.

$1^{st}$ Stage 6.2.1 197 gr SEC-EL was diluted 1:1 w/w with SAB, 10 mg/ml Benzyl Alcohol.

6.2.2 197 gr SEC-EL was diluted 1:1 w/w with SAB, 63.2 mg/ml Arginine.

6.2.3 197 gr SEC-EL was diluted 1:1 w/w with SAB, 600 mM mannitol.

6.2.4 197 gr SEC-EL was diluted 1:1 w/w with SAB, 54.8 mg/ml Lysine 6.2.5 92 gr SEC-EL was diluted with 208 gr SAB in order to prepare a solution containing 0.5 mg/ml r-h IFN-beta 1a. After filtration the solutions were divided into two 250 ml tubes containing 130 gr bulk) and six 2 ml tubes (containing 0.5 ml bulk).

One 250 ml tube and two 2 ml tubes were frozen and stored at −70° C.

One 250 ml tube and two 2 ml tubes were frozen at −70° C. and then transferred to a $2^{nd}$ freezer for storage at −20° C.

Two 2 ml tubes were stored at 2-8° C.

The SEC-EL was diluted with water in order to prepare 6 ml of a solution containing 0.088 mg/ml r-h IFN-beta 1a in 10 mM acetate pH-3.8.

$2^{nd}$ Stage

The following solutions were prepared at a concentration of 0.5 mg/ml r-h IFN-beta 1a.

6.2.6 The solution prepared in 6.2.1 was diluted with SAB, 5 mg/ml Benzyl Alcohol.

6.2.7 The solution prepared in 6.2.2 was diluted with SAB, 31.6 mg/ml Arginine.

6.2.8 The solution prepared in 6.2.3 was diluted with SAB, 300 mM mannitol.
6.2.9 The solution prepared in 6.2.4 was diluted with SAB, 27.4 mg/ml Lysine.
6.2.10 After filtration, these 4 solutions (6.2.6 to 6.2.9) were divided into four 250 ml tubes (containing 130 gr bulk) and six 2 ml tubes (containing 2 ml bulk). Total—fourteen 250 ml tubes and eighteen 2 ml tubes.
The remaining volume of these three solutions was further processed ($3^{rd}$ stage).
6.2.11 Two 250 ml tubes and two 2 ml tubes from each solution were frozen and stored at −70° C.
Two 250 ml tubes and two 2 ml tubes from each solution were frozen at −70° C. and then transferred to a $2^{nd}$ freezer for storage at −20° C.
Two 2 ml tubes from each solution were stored at 2-8° C.
$3^{rd}$ Stage (Dilution 1:100)
6.2.12 29.7 ml of the solution prepared in 6.2.6 was diluted with 0.3 ml of SAB, 5 mg/ml Benzyl Alcohol, 12 mg/ml Methionine.
6.2.13 29.7 ml of the solution prepared in 6.2.6 was diluted with 0.3 ml SAB, 5 mg/ml Benzyl Alcohol, 12 mg/ml Methionine, 50 mg/ml pluronic.
6.2.14 29.7 ml of the solution prepared in 6.2.6 was diluted with 0.3 ml SAB, 5 mg/ml Benzyl Alcohol, 12 mg/ml Methionine, 5 mg/ml TWEEN 20.
6.2.15 29.7 ml of the solution prepared in 6.2.7 was diluted with 0.3 ml SAB, 31.6 mg/ml Arginine, 12 mg/ml Methionine.
6.2.16 29.7 ml of the solution prepared in 6.2.7 was diluted with 0.3 ml SAB, 31.6 mg/ml Arginine, 12 mg/ml Methionine, 50 mg/ml pluronic.
6.2.17 29.7 ml of the solution prepared in 6.2.7 was diluted with 0.3 ml SAB, 31.6 mg/ml Arginine, 12 mg/ml Methionine, 5 mg/ml TWEEN 20.
6.2.18 29.7 ml of the solution prepared in 6.2.8 was diluted with 0.3 ml SAB, 300 mM mannitol, 12 mg/ml Methionine.
6.2.19 29.7 ml of the solution prepared in 6.2.8 was diluted with 0.3 ml SAB, 300 mM mannitol, 12 mg/ml Methionine, 50 mg/ml pluronic.
6.2.20 29.7 ml of the solution prepared in 6.2.8 was diluted with 0.3 ml SAB, 300 mM mannitol, 12 mg/ml Methionine, 5 mg/ml TWEEN 20.
6.2.21 29.7 ml of the solution prepared in 6.2.9 was diluted with 0.3 ml SAB, 27.4 mg/ml Lysine, 12 mg/ml Methionine.
6.2.22 29.7 ml of the solution prepared in 6.2.9 was diluted with 0.3 ml SAB, 27.4 mg/ml Lysine, 12 mg/ml Methionine, 50 mg/ml pluronic.
6.2.23 29.7 ml of the solution prepared in 6.2.9 was diluted with 0.3 ml SAB, 27.4 mg/ml Lysine, 12 mg/ml Methionine, 5 mg/ml TWEEN 20.
6.2.24 All the solutions (6.2.12 to 6.2.23) were filtered separately on a Millex syringe driven 0.2μ filter.
6.2.25 The solutions were divided into 2 ml tubes (at least 6 tubes for each solution).
6.2.26 Two 2 ml tubes from each solution were frozen and stored at −70° C.
Two 2 ml tubes from each solution were frozen at −70° C. and then transferred to a $2^{nd}$ freezer for storage at −20° C.
Two 2 ml tubes from each solution were stored at 2-8° C.

6.3 Bulk Analysis

One 2 ml tube stored at 2-8° C., −70° C. and −20° C. from each preformulation condition was analysed by SE-HPLC after thawing at room temp for 2 hours. Samples stored at −20° C. were transferred back to −70° C. for 4 hours before thawing. Results are shown in table 17.

One 250 ml tube stored at −70° C. from conditions 1, 5, 9, 13 and 15 (see Table 1) was analysed by SE-HPLC after thawing at room temp for 6 hours. Results are shown in table 18.

In addition, thermal dissociation studies were performed with samples in 15 ml tubes after 1 F/T cycle at an incubation temperature of 29° C. during 8 hours (1 ml samples from the 250 ml tubes after F/Tx1) and analysed by SE-HPLC (see table 19 for results).

7.0 Results

TABLE 17

Preformulation Results for Nunc tubes (0.5 ml) stored at −70° C., −20° C. and 2-8° C.

| | STORAGE CONDITIONS | | | | | |
| --- | --- | --- | --- | --- | --- | --- |
| | 2-8° C.* | | −20° C.** | | −70° C. | |
| CONDITION | % MONO | % AGG | % MONO | % AGG | % MONO | % AGG |
| 1 BA | 98.8 | 1.1 | 97.3 | 0.83 | 97.8 | 0.89 |
| 2 BA, MET | 99 | 0.94 | 97.7 | 0.84 | 98.1 | 0.78 |
| 3 BA, MET, TW | 98.7 | 0.14 | 98.9 | 0.85 | 99.1 | 0.84 |
| 4 BA, MET, POL | 98.9 | 1.0 | 97.3 | 0.93 | 98.1 | 0.71 |
| 5 ARG | 99.1 | 0.53 | 83.4 | 7.1 | 98.9 | 0.58 |
| 6 ARG, MET | 98.9 | 0.52 | 84.6 | 5.1 | 98.8 | 0.66 |
| 7 ARG, MET, TW | 98.6 | 0.8 | 97.5 | 2.5 | 99 | 0.49 |
| 8 ARG, MET, POL | 98.9 | 0.7 | 76.6 | 12.1 | 98.9 | 0.43 |
| 9 MAN | 99.9 | 0.05 | 81.2 | 1.3 | 97.8 | 0 |

TABLE 17-continued

Preformulation Results for Nunc tubes (0.5 ml) stored at −70° C., −20° C. and 2-8° C.

| | STORAGE CONDITIONS | | | | | |
|---|---|---|---|---|---|---|
| | 2-8° C.* | | −20° C.** | | −70° C. | |
| CONDITION | % MONO | % AGG | % MONO | % AGG | % MONO | % AGG |
| 10<br>MAN, MET | 100 | 0 | 83.5 | 0.97 | 98.2 | 0 |
| 11<br>MAN, MET, TW | 100 | 0 | 98.1 | 0.26 | 99.9 | 0 |
| 12<br>MAN, MET, POL | 100 | 0 | 83.3 | 1.1 | 87.5 | 0.68 |
| 13<br>50 mM acetate<br>CONTROL | 100 | 0 | 80.9 | 2.7 | 84 | 0.75 |
| 14<br>10 mM acetate | 100 | 0 | 89 | 0 | 92.4 | 0.82 |
| 15<br>LYS | 99.6 | 0 | 97.4 | 0 | 99.6 | 0.08 |
| 16<br>LYS, MET | 99.4 | 0 | 99.4 | 0 | 99.4 | 0.03 |
| 17<br>LYS, MET, TW | 99.1 | 0.18 | 99.4 | 0.23 | 99.6 | 0.13 |
| 18<br>LYS, MET, POL | 99.5 | 0.24 | 86.7 | 2.3 | 96.7 | 0.59 |
| ONLY TWEEN 20 | — | — | — | — | 99.8 | 0.13 |

*Stored at 2-8° C. for 3 weeks.
**Frozen at −70° C. stored at −20° C. for 16 days and transferred back to −70° C. for 4 hours. Results are the average of duplicates.
Bulk Buffer contained 50 mM sodium acetate pH-3.8 + excipients in different combinations (BA—Benzyl alcohol, MET—Methionine, MAN—Mannitol, TW—TWEEN 20, POL—Poloxamer)

TABLE 18

Preformulation Results for 250 ml tubes stored at −70° C. with (+INC) or without incubation at 29° C. for 8 hours

| Condition | Benzyl alcohol | L-Arg HCl | Mannitol | Lysine | Poloxamer 188 | Tween 20 | L-Met | % Mono | % Agg | % Dim |
|---|---|---|---|---|---|---|---|---|---|---|
| 1-nunc | √ | — | — | — | — | — | — | 96.2 | 1.1 | 2.7 |
| 1-(250 ml tube) | √ | — | — | — | — | — | — | 95.2 | 1.2 | 3.5 |
| 1-(250 ml tube) + INC | √ | — | — | — | — | — | — | 97.6 | 1.08 | 1.3 |
| 5-nunc | — | √ | — | — | — | — | — | 98.2 | 0.81 | 1.0 |
| 5-(250 ml tube) | — | √ | — | — | — | — | — | 98.5 | 0.41 | 1.1 |
| 5-(250 ml tube) + INC | — | √ | — | — | — | — | — | 99.46 | 0.58 | 0 |
| 9-nunc | — | — | √ | — | — | — | — | 97.4 | 0 | 2.6 |
| 9-(250 ml tube) | — | — | √ | — | — | — | — | 78.1 | 0.52 | 21.4 |
| 9-(250 ml tube) + INC | — | — | √ | — | — | — | — | 95.1 | 0 | 4.9 |
| 13-nunc Control | — | — | — | — | — | — | — | 82.1 | 1.2 | 16.6 |
| 13 Control (250 ml tube) | — | — | — | — | — | — | — | 73.2 | 2.2 | 24.5 |
| 13 Control (250 ml tube) + INC | — | — | — | — | — | — | — | 95.1 | 1.12 | 3.8 |
| 15-nunc | — | — | — | √ | — | — | — | 99.6 | 0.02 | 0.42 |
| 15-(250 ml tube) | — | — | — | √ | — | — | — | 99.4 | 0.03 | 0.61 |
| 15-(250 ml tube) + INC | — | — | — | √ | — | — | — | 99.9 | 0.11 | 0 |

TABLE 18-continued

Preformulation Results for 250 ml tubes stored at −70° C. with (+INC) or without incubation at 29° C. for 8 hours

| Condition | Benzyl alcohol | L-Arg HCl | Mannitol | Lysine | Poloxamer 188 | Tween 20 | L-Met | % Mono | % Agg | % Dim |
|---|---|---|---|---|---|---|---|---|---|---|
| Tween 20 Nunc | — | — | — | — | — | √ | — | 98.1 | 0 | 1.84 |
| Tween 20 Nunc + INC | — | — | — | — | — | √ | — | 99.8 | 0.04 | 0.13 |

Results are the average of duplicates

TABLE 19

Thermal dissociation in 15 ml tubes after 1 F/T cycle.

| Additive | Condition | Monomer | Dimer | aggregate |
|---|---|---|---|---|
| Benzyl alcohol | Before incubation | 94.76 | 4.08 | 1.17 |
|  | After 8 hours 29 C. | 97.58 | 1.34 | 1.08 |
| Arginine | Before incubation | 98.02 | 1.42 | 0.56 |
|  | After 8 hours 29 C. | 99.43 | 0 | 0.58 |
| Mannitol | Before incubation | 78.29 | 21.72 | 0 |
|  | After 8 hours 29 C. | 95.08 | 4.93 | 0 |
| Lysine | Before incubation | 99.3 | 0.62 | 0.09 |
|  | After 8 hours 29 C. | 99.89 | 0 | 0.11 |
| Tween 20 | Before incubation | 98.15 | 1.84 | 0 |
|  | After 8 hours 29 C. | 99.82 | 0.13 | 0.04 |
| Control | Before incubation | 73.4 | 24.67 | 1.93 |
|  | After 8 hours 29 C. | 95.09 | 3.79 | 1.12 |

8.0 Observations

Addition of excipient(s) to a bulk r-h interferon-beta 1a decreases consistently the percentage of dimers and aggregates (thus increases consistently the monomer percentage). Comparing the effects of thermal dissociation and selected excipients on r-h interferon beta, a slightly higher monomer level (lower dimer and aggregate level) can be achieved by the addition of excipients. In addition, preformulations stabilized by excipients show even higher monomer levels when further subject to thermal dissociation (e.g. incubation at 29° C.).

1. 2 ml tubes

At 4° C.

Small differences of % monomer in the various conditions are obtained (maximum delta 1.3%), and samples containing mannitol had the highest monomer level (100%).

At −70° C.

The combination Mannitol+TWEEN 20+Methionine is slightly better than lysine.

All stabilizers in various combinations can yield a % monomer ≧99.

At −70° C. and storage at −20° C.

The highest % monomer is obtained with a combination of Lysine+Tween Lysine+TWEEN 20+Methionine 2. 250 ml Tubes At −70° C.

There's a clear advantage to Lysine in lowering the oligomerization level compared to the other excipients tested.

Example 3

Stabilization of Interferon-Beta by the Addition of an Excipient to a Bulk-Interferon Analysed by Velocity Ultracentrifugation. SEC and Deg/Ox HPLC 1.0 Glossary/Abbreviations

| Agg | Aggregates |
|---|---|
| Dim | Dimers |
| Deg | Degradants |
| FDF | Final dosage form |
| F/T | Freezing and thawing |
| r-h IFN-beta 1a | Recombinant human interferon-beta 1a (r-h IFN-beta 1a) from CHO cells. |
| r-h IFN-beta FDF | r-h IFN-beta 1a final dosage form (r-h IFN-beta FDF) |
| SE-HPLC | Size exclusion high performance liquid chromatography |
| SAB | 50 mM sodium acetate pH-3.8 |
| Temp. | Temperature |

1.0 Introduction

The study was focused on minimization of oligomerization of r-h IFN-beta 1a during manufacturing steps from the SEC-EL fraction to the FDF storage in order to provide a stabilized bulk interferon.

Minimizing oligomerization was done by:

1) Pre-formulating the bulk with excipients and/or other stabilizing agents before freezing at −70° C.
2) Pre-formulating the bulk with excipients and/or other stabilizing without freezing and shipping at 2-8° C.
3) Shipping at 2-8° C. unfrozen r-h IFN-beta 1a bulk without preformulating.

The preformulated bulk samples were analyzed using SE-HPLC Deg/Ox HPLC and velocity ultracentrifugation methods. SE-HPLC is likely to detect only covalent oligomers whereas velocity ultracentrifugation also detects non-covalent oligomers both quantitatively and qualitatively.

3.0 Purpose/Scope

To minimize the oligomerization of r-h interferon-beta 1a during bulk processing.

4.0 Equipment and Materials

4.1 Equipment
0.2μ filter unit P/N MPGL025 Millipore
Revco freezer at −70° C.
Peristaltic pump
250 ml conical centrifuge tubes—Corning
1.8 ml cryotubes—Nunc

4.2 Materials
SEC el2 fraction
D-Mannitol DAB, Ph Eur, BP, USP, FCC, E421 (code 1.05980, Merck)
Glacial acetic acid 100% (code 1.00063, Merck),
Sodium hydroxide 10M
L-Methionine (1.05707, Merck)
L-Arginine monohydrochloride (code 1.01544, Merck)
Lysine (code 1.05701, Merck)

5.0 Procedure
The study was carried out on a SEC-EL2 fraction.
The outline scheme of the study is shown in FIG. 8.
The different preformulation conditions are shown in table 20.

TABLE 20

Preformulation conditions

| Condition | L-Arginine mg/ml | Mannitol mM | Lysine mg/ml | L-Methionine mg/ml | No of Tubes | Storage | Final pH | mg/ml* |
|---|---|---|---|---|---|---|---|---|
| 1 Control | — | — | — | — | 1 × 250 ml full<br>1 × 2 ml full<br>1 × 2 ml half full<br>1 × 250 ml<br>2 × 2 ml | 2-8° C.<br><br><br><br>−70° C. | 3.9 | 495 |
| 2 | 31.6 | — | — | — | 1 × 250 ml<br>4 × 2 ml | −70° C. | 3.83 | 420 |
| 3 | — | 300 | — | 0.12 | 2 × 250 ml full<br>4 × 2 ml | 2-8° C. | 3.92 | 507 |
| 4 | — | — | 82.2 | — | 2 × 250 ml<br>4 × 2 ml | −70° C. | 3.95 | 437 |

*tested by quant-HPLC

6.4 Preparation of Solutions
Solutions were prepared according to example 2.
1. Preparation of 50 mM sodium acetate pH-3.8 (SAB) See example 2.
2. Preparation of 0.5 liter 50 mM acetate pH-3.8, 63.2 mg/ml Arginine
   a. 0.483 kg WFI was weighted.
   b. 31.6 gr arginine was added.
   c. The solution was mixed for 5 minutes to allow the arginine to dissolve.
   d. 1.5 gr acetic acid was added.
   e. The solution was mixed for 5 minutes.
   f. While measuring pH, approximately 0.28 ml NaOH 10M was added until pH reached 3.8.
   g. The solution was sampled for conductivity and pH.
   h. The solution was filtered through a 0.2 micron filter.
3. Preparation of 1 liter 50 mM Acetate pH-3.8, 31.6 mg/ml Arginine
   a. 0.986 kg WFI was weighted.
   b. 31.6 gr arginine was added.
   c. The solution was mixed for 5 minutes to allow the arginine to dissolve.
   d. 3.002 gr acetic acid was added.
   e. The solution was mixed for 5 min.
   f. While measuring pH, approximately 0.56 ml NaOH 10M was added until pH reached 3.8.
   g. The solution was sampled for conductivity and pH.
   h. The solution was filtered through a 0.2 micron filter.
4. Preparation of 1 liter 50 mM acetate pH-4.1, 164.4. mg/ml Lysine
   a. 0.835 kg WFI was weighed.
   b. 164.4 gr lysine was added.
   c. The solution was mixed for 5 minutes to allow the lysine to dissolve.
   d. 3.002 gr acetic acid was added.
   e. The solution was mixed for 5 min.
   f. 0.56 ml NaOH 10M was added, the pH reached approximately 4.1.
   g. The solution was sampled for conductivity and pH.
   h. The solution was filtered through a 0.2 micron filter.
5. Preparation of 1 liter 50 mM acetate pH-4.0, 82.2. mg/ml Lysine
   a. 0.92 kg WFI was weighted.
   b. 82.2. gr lysine was added.
   c. The solution was mixed for 5 minutes to allow the lysine to dissolve.
   d. 3.002 gr acetic acid was added.
   e. The solution was mixed for 5 min.
   f. 0.56 ml NaOH 10M was added, the pH reached approximately 4.0.
   g. The solution was sampled for conductivity and pH.
   h. The solution was filtered through a 0.2 micron filter.
6. Preparation of 1 liter 50 mM acetate pH-3.8, 600 mM mannitol, 0.24 mg/ml methionine
   a. 0.92 kg WFI was weighted.
   b. 110.28. gr mannitol was added.
   c. The solution was mixed for 5 minutes to allow the mannitol to dissolve.
   d. 3.002 gr acetic acid was added.
   e. The solution was mixed for 5 min.
   f. 0.24 gr methionine was added.
   g. The solution was mixed for 5 min.

h. While measuring pH approximately 0.56 ml NaOH 10M was added until pH reached 3.8.
i. The solution was sampled for conductivity and pH.
j. The solution was filtered through a 0.2 micron filter.

7. Preparation of 2 liter 50 mM acetate pH-3.8, 300 mM mannitol 0.12 mg/ml methionine
  a. 1.93 kg WFI was weighted.
  b. 110.28. gr mannitol was added.
  c. The solution was mixed for 5 minutes to allow the mannitol to dissolve.
  d. 6.006 gr acetic acid was added.
  e. The solution was mixed for 5 min.
  f. 0.24 gr methionine was added.
  g. The solution was mixed for 5 min.
  h. While measuring pH approximately 1.12 ml NaOH 10M was added until pH reached 3.8.
  i. The solution was sampled for conductivity and pH.
  j. The solution was filtered through a 0.2 micron filter.

6.1 Bulk Preformulation

The outline scheme of the bulk preformulation and composition is shown in FIG. 8 and Table 20. The following is a detailed description of the preformulations.

The SEC-EL was quantitated by OD280, the concentration was 1.31 mg/ml.

$1^{st}$ Stage (SEC-EL2 Dilution 1:1 w/w with the Different Buffers)

6.2.1 An amount of 155 gr SEC-EL was diluted 1:1 w/w with 155 gr SAB, 164.4 mg/ml Lysine.
6.2.2 An amount of 78 gr SEC-EL was diluted 1:1 w/w with 78 gr SAB, 63.2 mg/ml Arginine.
6.2.3 An amount of 220 gr SEC-EL was diluted 1:1 w/w with 220 gr SAB, 600 mM mannitol, 0.24 mg/ml methionine.
6.2.4 An amount of 189 gr SEC-EL was diluted with 306 gr SAB in order to prepare a solution containing 0.50-mg/ml r-h IFN-beta 1a. After filtration this solution was divided into 250 ml tubes and 2 ml nunc tubes and stored at −70° C. or 2-8° C., 250 ml tubes for shipment at 2-8° C. were filled up to the cap.

$2^{nd}$ Stage (Final Bulk Dilution to 0.50-0.58 mg/ml r-h IFN-beta 1a)

The following solutions were prepared (the target concentration was 0.5 mg/ml r-h IFN-beta 1a).

6.2.5 310 gr of the solution prepared in 6.2.1 was diluted with 90 gr SAB, 82.4. mg/ml Lysine.
6.2.6 156 gr of the solution prepared in 6.2.2 was diluted with 48 gr SAB, 31.6 mg/ml Arginine.
6.2.7 440 gr of the solution prepared in 6.2.3 was diluted with 132 gr SAB, 300 mM mannitol, 0.12 mg/ml methionine.
6.2.8 After filtration these 3 solutions (6.2.5 to 6.2.7) were divided into 250 ml tubes.
and 2 ml tubes (containing 2 ml bulk).
6.2.9 250 ml tubes and 2 ml tubes of solutions containing lysine and arginine were frozen and stored at −70° C., the solution containing mannitol and methionine was stored at 2-8° C. (the 250 ml tube was filled up to the cap).

6.3 Preformulated Bulk Treatment

Samples stored at −70° C. and 2-8° C. were tested by velocity ultra centrifugation, Deg/Ox HPLC and SE-HPLC.

7.0 Results

TABLE 21

| Condition | L-Arginine mg/ml | Lysine mg/ml | Mannitol mM | Met mg/ml | Storage | pH | % Mono | % Agg | % Dimer | DEG/OX HPLC |
|---|---|---|---|---|---|---|---|---|---|---|
| 1 Control SEC-HPLC | — | — | — | — | −70° C. | 3.9 | 77.6 | 1.6 | 20.8 | 1.1 |
| 1 Control AUC | — | — | — | — |  |  | 80.4 | 2.2 | 17.4 |  |
| 1 Control SEC-HPLC | — | — | — | — | 2-8° C. |  | 99.9 |  |  | 1.1 |
| 1 Control AUC | — | — | — | — | 2-8° C. |  | 95 |  |  |  |
| 2 SEC-HPLC | 31.6 | — | — | — | −70° C. | 3.83 | 99 | 0 | 1 | 1 |
| 2 AUC | 31.6 | — | — | — | −70° C. |  | 96.6 | 0.7 | 2.7 |  |
| 3 SEC-HPLC | — | — | 300 | 0.12 | 2-8 C. | 3.92 | 99.8 | 0.2 | 0 | 1.1 |
| 3 AUC | — | — | 300 | 0.12 | 2-8 C. |  | 95 | 0.6 | 4.4 |  |
| 4 SEC-HPLC | — | 82.2 | 300 | 0.12 | −70° C. | 3.95 | 99.6 | 0.4 | 0 | 1.1 |
| 4 AUC | — | 82.2 | 300 | 0.12 | −70° C. | 3.95 | 93.8 | 0.6 | 5.6 |  |

8.0 Observations

The results obtained in example 2 are confirmed in the present study by both velocity ultracentrifugation and SEC methods (the differences in % monomer level being due to the likely detection of only covalent oligomers by SEC). In addition, DEG/OX HPLC indicate that level of oxidized forms remain stable after addition of excipients to the bulk r-h interferon beta 1a.

Example 4

Stabilization of Interferon-Beta by the Addition of an Excipient to a Bulk-Interferon Either Before or after Filtration Step 1.0 Glossary/Abbreviations

| | |
|---|---|
| Agg | Aggregates |
| COA | Certificate of analysis. |
| Dim | Dimers |
| Deg | Degradants |
| Deg/Ox-HPLC | Reverse phase high performance liquid chromatography for degradants and oxidized forms |
| F/T | Freezing and thawing |
| Quant-HPLC | Reverse phase high performance liquid chromatography for quantitative determination of r-IFNβ in r-h IFN-beta 1a bulk |
| r-h IFN-beta 1a | Recombinant human interferon-beta 1a (r-h IFN-beta 1a) from CHO cells. |
| r-h IFN-beta FDF | r-h IFN-beta 1a final dosage form (r-h IFN-beta FDF) |
| SE-HPLC | Size exclusion high performance liquid chromatography |
| Temp. | Temperature |

2.0 Summary

Using both SE-HPLC and velocity ultracentrifugation methods it was shown that preformulating IFN-β-1a bulk with 300 mM Mannitol (before freezing) minimizes covalent and non covalent oligomers and aggregates when added before or after bulk filtration and following 1 F/T and 4 F/T cycles.

The effect of addition of 300 mM Mannitol before filtration is more considerable in lowering the level of oligomerization, especially of the non covalent oligomers and aggregates in the 250 ml tubes (routine containers of the r-h IFN-beta 1a bulk).

Using both SE-HPLC and velocity ultracentrifugation methods it was shown that oligomers are not formed in unfrozen r-h IFN-beta 1a bulk stored at 2-8° C. but are formed during the freezing and thawing of the r-h IFN-beta 1a bulk.

3.0 Introduction

The minimization of oligomerization and aggregation of r-h IFN-beta 1a during freeze thaw cycles is a desired goal since it is believed that protein aggregates can elicit immunogenic reactions leading to the production of neutralizing antibodies.

The analytical method currently used for the determination of the level of monomers in the bulk is the SE-HPLC. Preliminary results using velocity ultracentrifugation seem to indicate that the SE-HPLC can detect only covalent oligomers whereas velocity ultracentrifugation, also detects non-covalent oligomers both quantitatively and qualitatively (see experiment 2). The proposed study was intended to determine the effect of preformulating the bulk with Mannitol in production scale on r-h IFN-beta 1a oligomerization and aggregation using both the SE-HPLC and the velocity ultracentrifugation methods as analytical methods.

4.1 Purpose/Scope 4.1.1 To determine if non covalent aggregates are present in the SEC fraction (before filtration and before freezing).

4.1.2 To determine if Mannitol at 300 mM minimizes covalent and non covalent oligomers and aggregates when added before or after bulk filtration, before freezing and following 1 F/T and 4 F/T cycles.

4.1.3 To determine if Mannitol at 150 mM minimizes covalent and non covalent oligomers and aggregates when added before bulk filtration, before freezing and following 1 F/T and 4 F/T cycles.

4.1.4 To determine if the level of non covalent aggregates in 1.8 ml test tubes is similar to that in 250 ml tubes, following F/T.

5.0 Equipment and Materials 5.1 Equipment
  0.2μ filtration unit for 150-500 ml Nalgene.

5.2 Materials
  SEC el2 fraction—800 ml.
  Mannitol-Merck P/N 1.05980.9050
  50 mM acetate buffer pH3.8-IPL code S88RD600
  50 mM acetate buffer pH 3.8 with 300 mM Mannitol (54.6 g Mannitol/liter).
  50 mM acetate buffer pH3.8 with 600 mM Mannitol (109.39 Mannitol/liter).
  50 mM acetate buffer pH 3.8 with 150 mM Mannitol (27.3 g Mannitol/liter).
  250 ml conical centrifuge tubes—Corning P/N 430776
  1.8 ml cryotubes—Nunc tubes P/N 375418

6.0 Procedure

The study was carried out on a single SEC el2 fraction. (concentration 1.81 mg/ml, according to OD280).

6.1 Bulk Preparation
The bulks were prepared as follows:
(1) SEC el2 fraction
  A 1.8 ml tube was fully filled for velocity ultracentrifugation and shipped at 2-8° C.
(2) Control
  180 ml SEC el2 were filtered through a 0.2 μm filter followed by a filter wash with 720 ml 50 mM acetate, pH-3.8. The bulk was distributed into four 250 ml tubes (200 ml each) and into ten 1.8 ml cryotubes before freezing at −70° C. Two of the 1.8 ml tubes were not frozen. One of these two tubes fully filled was kept at 2-8° C. before velocity ultracentrifugation analysis.
  The bulk concentration was 350 μg/ml (according to quant-HPLC).
(3) 300 mM Mannitol added after filtration
  180 ml SEC el2 were filtered through a 0.2 μm filter, and then the filter washed with 180 ml 50 mM acetate, 600 mM Mannitol pH-3.8 and 540 ml of 50 mM acetate, 300 mM Mannitol, pH-3.8. The bulk was distributed into four 250 ml tubes (200 ml each) and into ten 1.8 ml cryotubes before freezing at −70° C. Two of the 1.8 ml tubes were not frozen. One of these two tubes fully filled was kept at 2-8° C. before velocity ultracentrifugation analysis. The final Mannitol concentration was 300 mM. The bulk concentration was 344 μg/ml (according to quant-HPLC).

(4) 150 mM mannitol added before filtration 200 ml SEC el2 were mixed with 200 ml 50 mM acetate, 300 mM Mannitol, 380 ml of this mixture were filtered through a 0.2 μm filter and then the filter washed with 570 ml of 50 mM acetate, 150 mM Mannitol, pH-3.8. The bulk was distributed into four 250 ml tubes (200 ml each) and into ten 1.8 ml cryotubes before freezing at −70° C. Two of the 1.8 ml tubes were not frozen. One of these two tubes fully filled was kept at 2-8° C. before velocity ultracentrifugation analysis. The final Mannitol concentration was 150 mM. The bulk concentration was 342 μg/ml (according to quant-HPLC).

(5) 300 mM mannitol added before filtration 200 ml SEC el2 were mixed with 200 ml 50 mM acetate, 600 mM Mannitol, 380 ml of this mixture were filtered through a 0.2 μm filter and then the filter washed with 400 ml of 50 mM acetate, 300 mM Mannitol. The bulk was distributed into four 250 ml tubes (200 ml each) and into ten 1.8 ml cryotubes before freezing at −70° C. Two of the 1.8 ml tubes were not frozen. One of these two tubes fully filled was kept at 2-8° C. before velocity ultracentrifugation analysis. The final Mannitol concentration was 300 mM. The bulk concentration was 342 μg/ml (according to quant-HPLC).

Note: The SEC column eluent was collected in four 1 liter glass bottles in parallel via a system of four electronically controlled valves which were opened alternatively every 5 minutes (controlled by a LCC500 controller). In the case where Mannitol was added to the SEC-EL2 fraction prior filtration, the SEC fraction and the Mannitol solutions (4) or (5) were gently mixed in the glass bottle online during elution from the SEC column. In the case where Mannitol was added after the SEC filtration (3), the Mannitol was added and filtered through the same filtration unit but following the SEC EL-2 fraction.

6.2 Freezing and Thawing

The 4 F/T cycles of the 250 ml tubes were carried out by freezing for at least 8 hours and thawing for 7 hours at room temperature. The tubes were then mixed after each thawing cycle by 25 inversions. The 4 F/T cycles of the 1.8 ml tubes were carried out by freezing for at least 8 hours and thawing for 2 hours. The tubes were mixed by 20 inversions before the next freezing cycle. From each bulk condition (2-5), two frozen 250 ml tubes and two 1.8 ml tubes deriving from the 1 F/T and 4 F/T treatments were kept for velocity ultracentrifugation. The other two tubes of 250 ml and 1.8 ml for each bulk condition were thawed and tested by SEC-HPLC.

The SE-HPLC test and the velocity ultracentrifugation were carried out on samples thawed for 24 hours+/−2 hours. Allowing first the Mannitol to dissolve.

TABLE 22

List of samples tested per SEC/bulk batch

| Sample description | Sample volume in tube | Test |
|---|---|---|
| SEC 2-8° C. (1) | 1.8 ml in 1.8 ml | Vel . . . ultra. |
| Bulk 2-8° C. (1) | 1.8 ml in 1.8 ml | Vel . . . ultra. |
| | 0.5 ml in 1.8 ml | SE-HPLC |
| Bulk 1 F/T (2) | 200 ml in 250 ml | Vel . . . ultra. |
| | 1.8 ml in 1.8 ml | Vel . . . ultra. |
| | 200 ml in 250 ml | SE-HPLC |
| | 0.5 ml in 1.8 ml | SE-HPLC |
| Bulk 4 F/T (2) | 200 ml in 250 ml | Vel . . . ultra. |
| | 1.8 ml in 1.8 ml | Vel . . . ultra. |

TABLE 22-continued

List of samples tested per SEC/bulk batch

| Sample description | Sample volume in tube | Test |
|---|---|---|
| | 200 ml in 250 ml | SE-HPLC |
| | 0.5 ml in 1.8 ml | SE-HPLC |
| Bulk 300 mM Mannitol. (added after SEC filtration) 2-8° C. (3) | 1.8 ml in 1.8 ml | Vel . . . ultra. |
| | 0.5 ml in 1.8 ml | SE-HPLC |
| Bulk 300 mM Mannitol. (added after SEC filtration) 1 F/T (3) | 200 ml in 250 ml | Vel . . . ultra. |
| | 1.8 ml in 1.8 ml | Vel . . . ultra. |
| | 200 ml in 250 ml | SE-HPLC |
| | 0.5 ml in 1.8 ml | SE-HPLC |
| Bulk 300 mM Mannitol. (added after SEC filtration) 4 F/T (3) | 200 ml in 250 ml | Vel . . . ultra. |
| | 1.8 ml in 1.8 ml | Vel . . . ultra. |
| | 200 ml in 250 ml | SE-HPLC |
| | 0.5 ml in 1.8 ml | SE-HPLC |
| Bulk 150 mM Mannitol. (added before SEC filtration) 2-8° C. (4) | 1.8 ml in 1.8 ml | Vel . . . ultra. |
| | 0.5 ml in 1.8 ml | SE-HPLC |
| Bulk 150 mM Mannitol. (added before SEC filtration) 1 F/T (4) | 200 ml in 250 ml | Vel . . . ultra. |
| | 1.8 ml in 1.8 ml | Vel . . . ultra. |
| | 200 ml in 250 ml | SE-HPLC |
| | 0.5 ml in 1.8 ml | SE-HPLC |
| | 0.5 ml in 1.8 ml | QUANT HPLC |
| Bulk 150 mM Mannitol. (added before SEC filtration) 4 F/T (4) | 200 ml in 250 ml | Vel . . . ultra. |
| | 1.8 ml in 1.8 ml | Vel . . . ultra. |
| | 200 ml in 250 ml | SE-HPLC |
| | 0.5 ml in 1.8 ml | SE-HPLC |
| Bulk 300 mM Mannitol. (add before SEC filtration) 2-8° C. (5) | 1.8 ml in 1.8 ml | Vel . . . ultra. |
| | 0.5 ml in 1.8 ml | SE-HPLC |
| Bulk 300 mM Mannitol. (added before SEC filtration) 1 F/T (5) | 200 ml in 250 ml | Vel . . . ultra. |
| | 1.8 ml in 1.8 ml | Vel . . . ultra. |
| | 200 ml in 250 ml | SE-HPLC |
| | 0.5 ml in 1.8 ml | SE-HPLC |
| Bulk 300 mM Mannitol. (added before SEC filtration) 4 F/T (5) | 200 ml in 250 ml | Vel . . . ultra. |
| | 1.8 ml in 1.8 ml | Vel . . . ultra. |
| | 200 ml in 250 ml | SE-HPLC |
| | 0.5 ml in 1.8 ml | SE-HPLC |
| Bulk buffer (50 mM acetate buffer) | 250 ml in 250 ml (5 tubes) | Chemscan |
| | 250 ml in 250 ml (5 tubes) | Plate method |

Note:
The numbers in brackets refer to the outline scheme.

7.0 Results 7.1 Using the SE-HPLC method, after 1 F/T, preformulating with Mannitol in all three conditions (3, 4 & 5) had a slight effect on decreasing the level of oligomerization both in 1.8 ml and 250 ml tubes (~0.4% higher purity compared to the control sample).

Using the ultra centrifugation method, after 1 F/T Mannitol in all three conditions (3, 4 & 5) had a significant effect on the level of oligomerization both in 1.8 ml and 250 ml tubes.

In 250 ml tubes (Table 25), adding 300 mM Mannitol before filtration (condition 5) had a more positive effect in lowering oligomerization compared to adding 300 mM Mannitol after filtration (condition 3).

In 1.8 ml tubes (Table 24), adding 300 mM Mannitol after filtration (condition 3) had a more positive effect in lowering oligomerization compared to adding Mannitol before filtration (condition 5).

7.2 Using the SE-HPLC method, after 4 F/T cycles (Table 26), Mannitol in all three conditions (3, 4 & 5) had a significant effect on the level of oligomerization in 1.8 ml tubes (~2.6% higher purity compared to the control sample when preformulating with 300 mM Mannitol).

Using the ultra centrifugation, after 4 F/T cycles, Mannitol in all three conditions (3, 4, & 5) had a significant effect on the level of oligomerization both in 1.8 ml and 250 ml tubes. However the positive effect is more dominant in the 1.8 ml tubes.

7.3 Using both the SE-HPLC and ultra centrifugation methods (Table 23), no oligomerization occurred in samples stored at 2-8° C. (not frozen).

7.4 According to both SE-HPLC and ultra centrifugation, the level of oligomerization was significantly higher in 250 ml tubes compared to 1.8 ml tubes.

Note: The results in brackets in tables 23 to 27 are related to % aggregates

TABLE 23

% purity of bulk in 1.8 ml tubes stored at 2-8° C.

| Test | Conditions | | | |
|---|---|---|---|---|
| | 2 No Mannitol Control | 4 150 mM Mannitol Added before filtration | 3 300 mM Mannitol Added after filtration | 5 300 mM Mannitol Added before filtration |
| SE-HPLC | 100 | 100 | 100 | 100 |
| Ultra Centrifugation | NA | NA | NA | NA |

TABLE 24

% purity of bulk in 1.8 ml tubes after 1 F/T cycle

| Test | Conditions | | | |
|---|---|---|---|---|
| | 2 No Mannitol Control | 4 150 mM Mannitol Added before filtration | 3 300 mM Mannitol Added after filtration | 5 300 mM Mannitol Added before filtration |
| SE-HPLC | 99.4 (0.5) | 99.7 (0.1) | 99.7 (0) | 99.8 (0.1) |
| Ultra Centrifugation | 84.6 (1.1) | 88.1 (0.5) | 96.6 (0.1) | 94 (0.9) |

TABLE 25

% purity of bulk in 250 ml tubes after 1 F/T cycle

| Test | | Conditions | | | |
|---|---|---|---|---|---|
| | | 2 No Mannitol Control | 4 150 mM Mannitol Added before filtration | 3 300 mM Mannitol Added after filtration | 5 300 mM Mannitol Added before filtration |
| SE-HPLC | 1* | 98.5 (0.1) | 98.6 (0.1) | 99 (0.1) | 98.8 (0.2) |
| | 2* | 98.5 (0.1) | 98.6 (0.1) | 98.9 (0.1) | 99 (0.1) |
| | Avg | 98.5 (0.1) | 98.6 (0.1) | 98.95 (0.1) | 98.9 (0.15) |
| Ultra Centrifugation | | 75.8 (2.35) | 78 (2.22) | 80.7 (1.05) | 86 (0.35) |

*Sampled from the same 250 ml tube

TABLE 26

% purity of bulk in 1.8 ml tubes after 4 F/T cycle

| Test | | Conditions | | | |
|---|---|---|---|---|---|
| | | 2 No Mannitol Control | 4 150 mM Mannitol Added before filtration | 3 300 mM Mannitol Added after filtration | 5 300 mM Mannitol Added before filtration |
| SE-HPLC | 1* | 96.3 (1.4) | 98.3 (0.4) | 99 (0.3) | 99 (0.3) |
| | 2* | 96.5 (1.5) | 98.3 (0.4) | 99.1 (0.2) | 98.8 (0.3) |
| | Avg | 96.4 (1.45) | 98.3 (0.4) | 99.05 (0.25) | 98.9 (0.3) |
| Ultra Centrifugation | | 77 (6.8) | 92.7 (0.9) | 84.6 (1.5) | 86.1 (0.7) |

*Samples from separate 1.8 ml tubes

TABLE 27

% purity of bulk in 250 ml tubes after 4 F/T cycles

| Test | | 2<br>No<br>Mannitol<br>Control | 4<br>150 mM Mannitol<br>Added before<br>filtration | 3<br>300 mM Mannitol<br>Added after<br>filtration | 5<br>300 mM Mannitol<br>Added before<br>filtration |
|---|---|---|---|---|---|
| SE-HPLC | 1* | 94 (2.1) | 93.8 (0.9) | 94.3 (1.5) | 93.8 (1.4) |
| | 2* | 94 (2.1) | 93.8 (1.0) | 94.3 (1.5) | 93.8 (1.5 |
| | Avg | 94 (2.1) | 93.8 (0.95) | 94.3 (1.5) | 93.8 (1.45) |
| Ultra Centrifugation | | 72 (6.29) | 74 (4.48) | 76.4 (3.63) | 76.6 (4.01) |

*Samples from a single tube 8.0 Conclusions 8.1 Using both SE-HPLC and velocity ultracentrifugation methods, preformulating r-h IFN-beta 1a bulk with 300 mM Mannitol (before freezing) minimizes covalent and non covalent oligomers and aggregates when added before or after bulk filtration, following 1 F/T and 4 F/T cycles. However the effect of addition of 300 mM Mannitol before filtration is more considerable in lowering the level of oligomerization, especially of the non covalent oligomers and aggregates in the 250 ml tubes (routine containers of the IFN-β-1a bulk).

The effect of preformulating the bulk with Mannitol on r-h IFN-beta 1a oligomerization and aggregation, following F/T in 1.8 ml test tubes is similar to that in 250 ml tubes (about 0.4% higher purity compared to the control sample when tested by SE-HPLC and about 13% higher when tested by the velocity ultracentrifugation).

8.2 Addition of Mannitol at 150 mM concentration minimizes as well covalent and non covalent oligomers and aggregates when added before bulk filtration, before freezing and following 1 F/T and 4 F/T cycles but the effect is less considerable when compared to the effect of 300 mM.

8.3 Using both SE-HPLC and velocity ultracentrifugation methods it was shown that oligomers are not formed in unfrozen r-h IFN-beta 1a bulk and SEC-EL stored at 2-8° C. but are formed during the freezing and thawing the r-h IFN-beta 1a bulk.

8.4 Preliminary results using velocity ultracentrifugation seem to indicate that SE-HPLC (in contrast to the NEW SEC) can detect only covalent oligomers whereas velocity ultracentrifugation, also detects non-covalent oligomers both quantitatively and qualitatively.

Samples stored at 4° C. (or 2-8° C.), which were not subject to F/T cycles, remain very stable (in terms of % Mon content). Without wishing to be bound to this theory, it is believed that the effect of stresses on the molecule, like freeze/thawing cycles, increases consistently the formation of interferon-beta oligomers. In samples stored at 4° C., best results are yielded by the combination of mannitol and methionine eventually with the complementary addition of benzylalcohol or TWEEN 20, which show thus no oligomerization in samples stored at 2-8° C. Preferably, the present method employs a combination of mannitol and methionine as stabilizers with the possibility to further add benzylalcohol or TWEEN 20. Lysine alone or in any combination is also a preferred excipient to be employed. A few excipients show a stabilizing activity against the stresses provoked by F/T cycles, i.e. Tween 20, benzylalcohol or lysine (i.e. these excipients have been shown to counteract freeze/thaw stresses). If the manufacturing process is subject to freeze/thaw cycles then preferred excipients such as TWEEN 20, benzylalcohol or lysine are preferably added to the bulk solution.

Thus, when F/T cycles occur during the manufacturing process preferred excipients and combinations thereof are also identified. Samples stored at −20° C. in the present invention were subject to many F/T cycles (the tubes were frozen first at −70° C. and then transferred to a second freezer for storage at −20° C. for 16 days. The samples were then transfer back to −70° C. for 4 hours before thawing.). According to above, TWEEN 20, benzylalcohol and lysine are preferably used as stabilizers when stresses like F/T cycles occur. As such, at any storage temperature (−70° C., −20° C. or 4° C.) and in the presence of F/T cycles stresses, Tween stresses, TWEEN 20, lysine and benzylalcohol alone or in any combination are the preferred excipients to be used in a bulk interferon solution. The following combinations are particularly preferred:

1. Lysine and benzylalcohol,
2. Lysine and TWEEN 20,
3. Lysine and benzylalcohol and TWEEN 20, and
4. Benzylalcohol and TWEEN 20. The embodiments described below are the most preferred ones for any storage temperature (−70° C., −20° C. or 4° C.) and in the presence of F/T cycles stresses.

Lysine yields very good results at −20° C., as well as for 4° C. and −70° C. in terms of % Mon and % Agg. Lysine is the only amino acid tested that is capable of stabilizing interferon-beta against freeze/thaw cycles. Thus, lysine is the most preferred excipient against F/T cycles and avoids requirement for bacteriostatic agents (e.g. benzylalcohol) or surfactants (e.g. TWEEN 20), which were the two other excipients showing stabilizing activity against F/T stress. As such, preformulations can be considered that only contain lysine or a combination of lysine and an antioxidant (e.g. methionine). Best results at −20° C. are in fact obtained by a combination of lysine and methionine. More preferably, the present invention employs a combination of lysine and methionine. A high level of monomer percentage is obtained with a combination of mannitol, methionine and TWEEN 20 (98.12% Mon). A combination of benzylalcohol and methionine yields a high monomer percentage (~98% Mon). Thus, a combination of benzylalcohol and methionine is preferred. TWEEN 20 can be further added to this combination, yielding a higher % monomer (~99%). Thus, a combination of benzylalcohol, methionine and TWEEN 20 is more preferred.

Experiments have been conducted at two specific points during the manufacturing processing. Addition of certain excipients (e.g. mannitol) before or after filtration lowers and/or reduces oligomers and aggregates formation. Using both SE-HPLC and velocity ultracentrifugation methods, preformulating r-h IFN-beta 1a bulk with 300 mM Mannitol (before freezing) minimizes covalent and non covalent oligomers and aggregates when added before or after bulk filtration, following 1 F/T and 4 F/T cycles. The invention should thus by no means be limited to only a specific point of the bulk protein manufacturing process but encompasses all the steps needed for the preparation and/or storage of a preformulated bulk protein (i.e. stabilizing excipients can be added at different multiple steps during the bulk processing). Results show no great difference in terms of oligomerization and aggregation, but addition of mannitol before filtration yields better results, especially of the non covalent oligomers and aggregates in 250 ml tubes. Preferably, mannitol is therefore added before filtration step.

Finally, the above experiments have shown that the combination of certain excipients and thermal dissociation can yield higher levels of monomer percentage compared to the levels obtained when taken separately. In this manner, drastic reduction in terms of dimers and aggregates levels are achieved. Thus, the present invention preferably combines a stabilized bulk solution by means of added excipients with thermal dissociation. Thermal dissociation can be performed at any stages of the manufacturing process and should by no means be limited to a specific point of the bulk processing.

Example 5

Preformulation Studies at pH 4.7

To evaluate pH incidence on oligomerization and aggregates formation, a preformulation study was performed at pH 4.7.

(1) Procedure:
1. A first bulk at approximately 0.5 mg/ml was preformulated to pH 4.7 by mixing 1:1 (1 volume of SEC E12 fraction with 1 volume of 50 mM acetate pH7.2, titrated with NaOH).
2. A second bulk was preformulated at pH 4.7 with lysine 82.2 mg/ml by mixing 1:1 (1 volume of SEC E12 fraction with 1 volume of 50 mM acetate pH7.2, containing lysine at 164.4 mg/ml titrated with NaOH).
3. These preparations were compared to a control at 0.5 mg/ml in 50 mM acetate pH 3.8 and to a preformulated control 0.5 mg/ml in 50 mM acetate pH 3.9 with 82.2 mg/ml lysine.
4. After one cycle of freeze thawing in 1.8 ml tubes, the samples were tested by the new SEC HPLC method.

Results:

TABLE 28

| Conditions | % monomer | % dimer | % aggregate |
| --- | --- | --- | --- |
| pH 3.8 | 81.41 | 17.92 | 0.67 |
| pH 4.7 | 99.1 | 0.9 | 0 |
| pH 4.7 | 99.4 | 0.6 | 0 |
| pH 4.7 + Lysine 82.2 mg/ml | 99.6 | 0.24 | 0.12 |
| pH 3.9 + Lysine 82.2 mg/ml | 99.7 | 0.03 | 0.27 |

(2) Conclusion:
Preformulation at pH 4.7 reduces consistently oligomerization and the formation of aggregates compared with preformulation at pH 3.8 (~99% Mon compared with ~81% Mon respectively and 0.67% aggregate with 0% aggregate respectively.). Thus, the method of the present invention is preferably accomplished at a pH of 4.7.

Preformulation with lysine at either pH 3.9 or pH 4.7 reduces oligomerization. At pH 4.7, addition of lysine yields a % Mon of 99.6 compared to 99.1% Mon without lysine. At pH 3.8, addition of lysine has a striking effect on reducing oligomerization yielding a % Mon of 99.7 compared with 81.41% Mon without lysine. Thus, lysine is a preferred amino acid to be added to the method of the present invention.

Combining preformulation at pH 4.7 and addition of lysine yields the best results. Thus, the method of the present invention is most preferably accomplished at a pH of 4.7 with the addition of lysine as an excipient. In a most preferred embodiment, the present method of the invention can therefore combine addition of preferred excipients to a bulk-interferon at pH 4.7 with thermal dissociation.

Example 6

Analytical Methods

The present example describes the different analytical methods used.

Size exclusion (SE)-HPLC, New SE-HPLC, herein also referred as "new SE-HPLC" or "NEW SEC", and velocity ultracentrigufation (AUC) were used for the measurement of aggregates' and oligomers' levels of recombinant human interferon-beta 1a (r-h IFN-beta 1a or r-hβIFN-1a). The NEW SE-HPLC and AUC methods presented are able to detect both covalent and non-covalent oligomers as well as aggregates both quantitatively and qualitatively.

a. SE-HPLC—Purity Test
SE-HPLC is used in order to determine the amount of aggregates in the IFN-β-1a bulk.

Procedure
100 μl samples of both the IFN-β-1a bulk to be examined and the control sample (PRB) are analyzed.
The following solution is prepared: 30% ACN (acetonitrile)/0.2% TFA (trifluoroacetic acid)/H$_2$O.
The column (Progel-TSK G2000 or equivalent) is equilibrated in the eluent, at a flow rate of 0.5 ml/min, for at least 1 hour. Once a steady baseline is obtained, samples of 100 μl are injected and eluted using an isocratic gradient, at a flow rate of 0.5 ml/min. The column profile is recorded by UV detection at 214 nm. The percentage of IFN-β-1a monomer of the bulk sample is determined from the protein peaks integrated areas.

Specification
The main peak area of IFN-β-1a bulk sample (corresponding to the intact molecule) is not less than 95% of the total peaks area, with not more than 1% of aggregates.

Procedure for Freeze/Thaw (F/T) Control Sample for the SE-HPLC Test
1. Withdraw the desired amount of r-h interferon-beta 1a bulk/batch from the −70° C. freezer.
2. Thaw at room temperature for 6 to 9 hours for large tube (~200 ml), or 2 to 4 hours for small tube/ampoule (1-15 ml). (First cycle of freeze/thaw).
3. A desirable quantity of above bulk is aliquot to 1 ml portions (in case of large tube).
4. Freeze the aliquots at −70° C. for at least 2 hours.
5. Repeat steps 2 and 4 for three more times.

6. After the fourth thawing cycle dilute the small amount of control sample to 0.25 mg/ml with dilution buffer for checking.
7. The aliquots should be stored at −70° C.
8. Thaw the control F/T aliquoted tubes for 2 hours at room temperature before using it in the SE-HPLC test.

b. NEW SE-HPLC

The detection of the total aggregates content is performed on a TSK G2000SWXL column (TosoHaas) or a BioSuite (Waters); the elution is performed in isocratic mode at 0.5 mL/min using 50 mM sodium acetate buffer, 50 mM NaCl pH 3.8; the wavelength is set at 215 nm. The runtime is 30 min. R-h IFN-beta 1a Bulk as it is (0.35 mg/ml) is injected in the column in the saturation phase (0.2 ml per injection).

Equipments and Materials of the New SE-HPLC Method:
HPLC system: Waters Alliance
UV detector: Waters 996 PDA wavelength 214 nm
Autosampler temperature setting: 4° C.
Column TosoHaas TSK G2000 $SW_{XL}$
Column temperature: room temperature
Mobile phase: 50 mM Sodium acetate pH 3.8 with 50 mM NaCl
Prepared by dissolving 5.84 gr NaCl in 2 liter 50 mM Sodium acetate pH 3.8 buffer. The acetate buffer was prepared at sterile solution unit by adding acetic acid to WFI and titrating with a solution of 10M NaOH up to pH-3.8.
Flow rate: 0.5 mL/min
Eluent: 50 mM $CH_3COONa$—50 mM NaCl, pH 3.8
Activating solution: 50 mM HCl—50 mM NaCl
Reagents:
Acetic, Merck code K31358056
NaOH, Merck B197582
NaOH 10M solution
WFI
NaCl, JT BAKER code 3627-07 c. Sedimentation Velocity Analysis—AUC

1. Method Description

Samples are loaded into cells with 2-channel charcoal-epon centrepieces with 12 mm optical pathlength. The centerpieces and sapphire windows are cleaned with detergent and then soaked in water to try to have the cleanest possible surfaces. The corresponding placebo is loaded in the reference channel (the instrument functions like a dual-beam spectrophotometer). Those loaded cells are then placed into an AN-50Ti analytical rotor, loaded into a Beckman Optima XL-I analytical centrifuge, and brought to 20° C. The rotor is then brought to 3000 rpm and the samples are scanned (at 280 nm, the absorbance peak) to confirm proper cell loading. The rotor is then brought to the final run speed of 50000 rpm. 50 scans for each sample are recorded at this rotor speed.

Data are analysed using the c(s) method developed by Peter Schuck at the N.I.H. and implemented in his analysis program SEDFIT (version 8.7; Schuck, P. (2000). Size-distribution analysis of macromolecules by sedimentation velocity ultracentrifugation and Lamm equation modelling. *Biophys. J.* 78, 1606-1619).

In this approach many raw data are directly fitted to derive the distribution of sedimentation coefficients, while modelling the influence of diffusion on the data in order to enhance the resolution. The method works by assigning a diffusion coefficient to each value of sedimentation coefficient based on an assumption that all species have the same overall hydrodynamic shape (with shape defined by the frictional coefficient ratio relative to that for a sphere, $f/f_0$). The $f/f_0$ values are then varied to find the best overall fit of the data for each sample. The distributions are calculated using 0.51 maximum-entropy smoothing.

2. Analytical Parameters

| | |
|---|---|
| Rotor type | 8-holes rotor |
| Rotor speed | 50k rpm |
| Centerpieces | charcoal epon |
| Channel length | 12 mm |
| Temperature during the AUC run | 20° C. |
| Detection wavelength | 280 nm |
| Sample volume | 432 mcl |
| Reference volume | 442 mcl |

3. Equipment and Software

Analytical Ultracentrifuge Model XL-I (Beckman Coulter)
SEDFIT ver 8.70b Software (Peter Schuck—National Institutes of Health)
Origin ver 6.03 Software (Beckman Coulter)
Proteome Lab XL-A/XL-1 ver 5.0 Software (Beckman Coulter)

d. IFN-β-1a Quantitation by RP-HPLC—QUANT-HPLC

The reverse phase method described below enables the quantification of IFN-ε-1a in bulk samples.

The quantification of the protein is performed on a C4, Wide-Pore Butyl 5 μm column (Baker); the wavelength is set at 214 nm and the elution is performed at 1 mL/min using the following mobile phase and gradient:

Procedure

The IFN-β-1a samples to be examined are diluted with 50 mM sodium acetate buffer, pH 3.8, to a concentration ranging between 50 and 150 μg/ml.

The following solutions are prepared:
Eluent A: 0.1% TFA in $H_2O$ (water/trifluoroacetic acid 0.1%)
Eluent B: 0.1% TFA in ACN (acetonitrile/trifluoroacetic acid 0.1%)
Eluent C: ACN (acetonitrile)

The C4 RP-HPLC column is first washed with Eluent C at a flow rate of 1.0 ml/min for 30 min and subsequently with 50% $H_2O$ and 50% ACN for 15 min. The column is equilibrated in 70% Eluent A and 30% Eluent B, at a flow rate of approximately 1.0 ml/min for 15 min.

Once a steady baseline is obtained, IFN-β-1a bulk samples, control samples and calibration curve samples (PRB, 1.24-19.8 μg) are sequentially injected. In each case 100 μl are injected except for the 1.24 μg sample of the calibration curve, for which 20 μl are injected. The flow rate is maintained at of 1.0 ml/min.

The following gradient is used:

TABLE 29

| Time (min.) | % Eluent A | % Eluent B | % Eluent C |
|---|---|---|---|
| 0 | 70 | 30 | 0 |
| 5.0 | 70 | 30 | 0 |
| 6.0 | 58 | 42 | 0 |
| 15.0 | 57 | 43 | 0 |
| 30.0 | 46 | 54 | 0 |
| 35.0 | 45 | 55 | 0 |
| 40.0 | 40 | 60 | 0 |
| 40.1 | 20 | 80 | 0 |

TABLE 29-continued

| Time (min.) | % Eluent A | % Eluent B | % Eluent C |
|---|---|---|---|
| 45.0 | 20 | 80 | 0 |
| 45.1 | 0 | 0 | 100 |
| 50.0 | 0 | 0 | 100 |
| 50.1 | 70 | 30 | 0 |
| 65.0 | 70 | 30 | 0 |

Runtime=65 min

The amount of IFN-β-1a in the test sample is calculated from the logarithmic regression of the calibration curve areas.

Specification

The IFN-β-1a bulk contains 0.280 to 0.500 mg IFN-β-1a/ml.

e. Purity by Reverse Phase (RP)-HPLC—DEG/OX

The reverse phase method described below enables the detection of IFN-β-1a oxidized forms, which elute differently from the intact molecule.

The quantification of the oxidised forms is performed on a C4, Supelcosil LC-304 column (Supelco) thermostated at 40° C.; the wavelength is set at 208 nm and the elution is performed at 1 mL/min using the following mobile phase and gradient:

The following solutions are prepared:
Eluent A: 60% $H_2O$/40% ACN/0.14% HFBA (water 60%/acetonitrile 40%/Heptafluorobutirric acid 0.14%)
Eluent B: 20% $H_2O$/80% ACN/0.14% HFBA (water 20%/Acetonitrile 80%/Heptafluorobutirric acid 0.14%)
Eluent C: 20% $H_2O$/80% ACN/0.1% TFA (water 20%/Acetonitrile 80%/Trifluoroacetic acid 0.1%)

The C4 RP-HPLC column is equilibrated with 70% Eluent A and 30% Eluent B, at a flow rate of 1 ml/min for at least 15 minutes (until a steady baseline is obtained). Samples of 120 μl are injected. The sample to be examined is diluted with 50 mM sodium acetate, pH 3.8, to a concentration ranging between 0.250 and 0.280 mg/ml.

The following gradient is used:

TABLE 30

| Time (min) | % Eluent A | % Eluent B | % Eluent C |
|---|---|---|---|
| 0 | 70 | 30 | 0 |
| 8 | 70 | 30 | 0 |
| 61 | 62 | 38 | 0 |
| 66 | 0 | 100 | 0 |
| 71 | 0 | 0 | 100 |
| 72 | 70 | 30 | 0 |

The percentage purity of the IFN-β-1a bulk sample is calculated using the protein peaks integrated areas.

Specification

The main peak area of IFN-β-1a (corresponding to the intact molecule) is not less than 95% of the total peaks area.

f. Cytopathic Effect Inhibition Bioassay—CPE

Biopotency (Antiviral Activity)

The antiviral activity of IFN-β-1a bulk is measured by the cytopathic effect (CPE) inhibition bioassay.

The biological activity is measured by an antiviral assay based on the IFN-β induced protection of cells (WISH cells-human amniotic tissue) against the cytopathic effect of a virus (Vesicular Stomatitis Virus).

The principle of the bioassay for interferon lies on the fact that a number of viruses such as Vesicular Stomatitis Virus (VSV) cause cell death that can be visualized by vital staining.

The cytopathic effect can then be used to quantify cell protection by interferon. The assay is performed by the indirect measure of cell death, which is assessed by the amounts of dye tetrazolium salt MTT (Dimethylthiotetrazolium) taken up by living cells. The method makes use of automatic spectrophotometric determination of the percent of protected cells and of a three point parallel line assay for the statistical evaluation of the titer.

Procedure

The assay is performed in microliter plates.
  a. 50 μl of cell culture medium (MEM/5% FBS) are added to each well.
  b. 100 μl of IFN-β-1a sample or standard solution (60-100 IU hIFN-β/ml) are added to the wells and three 1:1.5 step dilutions are performed from row to row in the plates.
  c. A 50 μl suspension of WISH cells ($0.78$-$0.82 \times 10^6$ cells/ml) is added to each well and the plates are incubated at 37° C. for 18-20 hours in a 5% $CO_2$ humidified incubator.
  d. A VSV suspension is added to each well except the cell control wells, filled with MEM/2.5% FBS.
  e. The plates are incubated for 24 hours in a 5% $CO_2$ humidified incubator at 37° C.
  f. After having verified by an inverted microscope that
    (1) at least 80% of cell damage is achieved in the VSV control row and
    (2) the percentage mean values of protection in presence of the IFN-β standard fall in the range of 84% for the non diluted standard, 45% for the 1:1.5 dilution, and 27% for the 1:3 dilution
  the cultures are stained with the specific dye MTT.
  g. The intensity of the coloration is determined by automatic spectrophotometric reading at 592 nm.
  h. To quantitate the IFN-β-1a activity, the OD readings are then analyzed by a computer program (Colombo Software).

Specification

The IFN-β-1a bulk contains not less than $50 \times 10^6$ IU/ml.

g. Carbohydrate Mapping by Electrospray Ionisation Mass Spectrometry—ES-MS

The carbohydrate moiety of IFN-β-1a, which is N-linked to the Asn-80 residue, is analyzed by ES-MS of the intact molecule using a quadrupole mass spectrometer.

Procedure

The test method consists of the following steps:
  1) Desalting of the IFN-β1a bulk sample,
  2) ES-MS semi-quantitative analysis of the intact glycoform species of IFN-β-1a using a quadrupole mass spectrometer.

The intact glycoforms are identified in the ES-MS spectrum according to their expected molecular weight (at the range of 21-24 kDa, where the protein chain MW is 20 kDa). Afterwards, the glycoforms are grouped according to their level of sialylation (non-sialylated, mono-sialylated, di-sialylated, tri-sialylated) and their relative % abundance is determined according to their relative peak heights.

Sample Desalting

About 35 μg IFN-β-1a samples (Control IFN-β1a sample and bulk test sample) are desalted by dialysis (Microcon 10 device, Amicon, or equivalent) versus acetonitrile/water/acetic acid (40/60/1, v/v) at room temperature (about 150 μg IFN-β-1a/ml final concentration).

ES-MS Analysis

Positive ionization ES-MS analysis is carried out on a Micromass Platform LCZ single quadrupole mass spectrometer (or equivalent) by direct inflow of the desalted samples with an infusion pump set at about 6-10 μl/min into the electrospray source.

The mass spectrometer is calibrated with myoglobin in the m/z range of 600-2400 Da and is run using the following settings:

| Capillary voltage: | 2.5-4.0 KV |
|---|---|
| Cone voltage: | 36 V |
| Source temperature: | 70-100° C. |

The mass acquisition is carried out by scanning from 600 Da to 2400 Da (for myoglobin) and 1100 to 2400 Da (for IFN-β1a) at a typical scan rate of about 10 sec/scan. Mass spectra processing and deconvolution of multiply charged ions is performed using the Mass Lynx software (or equivalent).

ES-MS Results Interpretation

A representative deconvoluted ES-MS spectrum shows that the MS peaks (termed A to F) represent distinct glycoforms that can be gathered into 4 major glycoform groups according to their degree of sialylation, as shown in the table 34 below.

TABLE 31

Glycoforms observed in the ES-MS spectrum of IFN-β-1a

| MS Peak | Glycoform* | Expected MW (Da) | Sialylation level |
|---|---|---|---|
| F | 2A0S1F | 21793 | Non-sialylated |
| B | 2A1S1F | 22084 | Mono-sialylated |
| A | 2A2S1F | 22375 | Di-sialylated |
| C | 3A2S1F and/or 2A2S1F + 1 HexNacHex repeat | 22739 | Di-sialylated |
| D | 3A3S1F | 23031 | Tri-sialylated |
| E | 4A3S1F and/or 3A3S1F + 1 HexNacHex repeat | 23400 | Tri-sialylated |

*2A = Biantennary complex type oligosaccharide; 3A = Triantennary complex type oligosaccharide; 4A = Tetrantennary complex type oligosaccharide; 0S = non-sialylated; 2S = Di-sialylated, 3S = Tri-sialylated, 1F = Fucosylated.

The semi-quantitative evaluation of each of the 4 major glycoforms is carried out as follows:
  % Nonsialylated glycoforms: Height of peak F/Total peak heights×1100
  % Monosialylated glycoforms: Height of peak B/Total peak heights×100
  % Disialylated glycoforms: Heights of peaks (A+C)/Total peak heights×100
  % Trisialylated glycoforms: Heights of peaks (D+E)/Total peak heights×100 with the total peak height being the sum of peak heights A to F.

Please note that the unlabelled MS peak at about 22244 Da (Figure SPA-1), corresponding to N-terminal truncated (2-166 aa) 2A2S1F IFN-β1a lacking one terminal methionine, is not taken into consideration for the calculation of the % di-sialylated glycoforms of IFN-β-1a, the levels of this impurity being controlled by a separate bulk purity release test (N-terminal truncation, N-1: NMT 6%).

Specification

Spectrum conforms to expected IFN-β-1a profile (% peak heights):

Non-sialylated glycoforms: Not more than 5%

Mono-sialylated glycoforms: 6-30%

Di-sialylated glycoforms: 56-81%

Tri-sialylated glycoforms: 8-16% h. Isoelectric Focusing—IEF

The IFN-β-1a isoforms are separated by isoelectric focusing and visualized by Coomassie blue staining. The pI of the isoforms is then compared to that of the PRB. The pI and the area of the glycoforms is measured by densitometry.

Procedure

Sample Preparation:

IFN-β-1a samples are concentrated to 0.7-1.0 mg/ml by using a centrifugal microcentrator unit.

Gel Preparation and Isoelectric Focusing:

An IEF 5% acrylamide gel is prepared and washed after casting in order to remove all unpolymerized acrylamide. The gel is then reconstituted with ampholytes (2% final, pH range 3-10), 10 mM glutamic acid, 10 mM lysine and 3% glycerol, placed into a horizontal electrophoresis apparatus and cooled to 15° C.

The gel is prefocused for 60 minutes at a power of 1 W under a nitrogen flow in presence of a carbon dioxide trap (0.1 M NaOH).

Approximately 3.5 μg of bulk IFN-β-1a, 6 μg of Cytochrome c and appropriate pI standards are then applied as drops (5 μl) on the surface of the gel.

The IEF gel is focused at 101° C. at 8000 V-hour.

The gel is fixed in 20% (w/v) TCA for 30-35 min, then stained with Coomassie blue by using the colloidal procedure of Neuhoff et al. (Neuhoff, V., Arold, N., Taube, D., Ehrhardt, W., Improved staining of proteins in polyacrylamide gels including isoelectric focusing gels with clear background at nanogram sensitivity using Coomassie Brilliant Blue G-250 and R-250, Electrophoresis, 1988:9:255-262).

The quantitation and pI determination of the IFN-β-1a isoforms is done using an automated densitometer (Computing Densitometer, Molecular Dynamics, USA, supplied with an ImageQuant 3.3 program and other specialized softwares needed for integration/calculation of results; or equivalent equipment).

Specification

The electrophoretogram obtained with the test sample is similar to that obtained with the reference house standard:
1. The electrophoretogram obtained consists of three main groups of bands, containing a total of 5 to 10 bands (excluding the band at the loading point) and conforms to the band pattern obtained with the reference standard.
2. The five major bands, assayed by densitometry, should fall within the groups limits shown in table 32

TABLE 32

| electric focusing, specification of the isoforms | | |
|---|---|---|
| Group n° | pI | % Total Area |
| 1 | 8.8-9.2 | 8-27 |
| 2 | 8.4-8.7 | 47-72 |
| 3 | 7.7-8.1 | 11-34 |

REFERENCES

1. Derynk R. et al., Nature 1980; 285, 542-547.
2. Familletti, P. C., Rubinstein, S., and Pestka, S. 1981 "A Convenient and Rapid Cytopathic Effect Inhibition Assay for Interferon," in Methods in Enzymology, Vol. 78 (S. Pestka, ed.), Academic Press, New York, 387-394;
3. Mark D. F. et al., Proc. Natl. Acad. Sci. U.S.A., 81 (18) 5662-5666 (1984).
4. Pestka, S. (1986) "Interferon Standards and General Abbreviations, in Methods in Enzymology (S. Pestka, ed.), Academic Press, New York 119, 14-23.
5. Rubinstein, S., Familletti, P. C., and Pestka, S. Convenient Assay for Interferons. J. Virol 1981; 37, 755-758.
6. Shepard H. M. et al., Nature 1981; 294, 563-565.

The invention claimed is:

1. A method of preparing a stabilized bulk solution of an IFN-beta protein, said method comprising the steps of:
   a) providing a bulk of IFN-beta protein in a buffer solution;
   b) adding an excipient to said bulk to form a stabilized bulk solution of IFN-beta protein, wherein said excipient is selected from the group consisting of:
      i) a bacteriostatic agent,
      ii) a surfactant,
      iii) an isotonicity agent,
      iv) an amino acid,
      v) an antioxidant,
      vi) an isotonicity agent and an antioxidant,
      vii) an isotonicity agent, an antioxidant and an amino acid,
      viii) an amino acid and an antioxidant,
      ix) an amino acid, an antioxidant and a surfactant,
      x) a bacteriostatic agent and an antioxidant, and
      xi) a bacteriostatic agent, an antioxidant and a surfactant; and
   c) incubating the bulk solution at a temperature range of 27° C. to 31° C. for about 3 hours to about 40 hours.

2. The method of claim 1, wherein the IFN-beta is recombinant human IFN-beta.

3. The method of claim 1, wherein the protein is stabilized against aggregation.

4. The method of claim 1, wherein the protein is stabilized against oligomerization.

5. The method of claim 1, wherein the bacteriostatic agent is benzylalcohol.

6. The method of claim 1, wherein the surfactant is polysorbate 20.

7. The method of claim 1, wherein the isotonicity agent is mannitol.

8. The method of claim 1, wherein the amino acid is lysine or arginine.

9. The method of claim 1, wherein the antioxidant is methionine.

10. The method of claim 1, wherein the isotonicity agent is mannitol and the antioxidant is methionine.

11. The method of claim 1, wherein the isotonicity agent is mannitol, the antioxidant is methionine and the amino acid is lysine.

12. The method of claim 1, wherein the amino acid is lysine and the antioxidant methionine.

13. The method of claim 1, wherein the amino acid is lysine, the antioxidant is methionine and the surfactant is polysorbate 20.

14. The method of claim 1, wherein the bacteriostatic agent is benzylalcohol and the antioxidant is methionine.

15. The method of claim 1, wherein the bacteriostatic agent is benzylalcohol, the antioxidant is methionine and the surfactant is polysorbate 20.

16. The method of claim 1, wherein said temperature is 29° C.

17. The method of claim 1, wherein such incubation is carried out before or after the step (b) of claim 1.

18. The method of claim 1, wherein said incubation is performed for a range of 6 hours to 40 hours.

19. The method of claim 1, wherein said incubation is performed for a range of 15 hours to 30 hours.

20. The method of claim 1, wherein said IFN-beta is present at a concentration of about 10 μg/ml to about 2000 μg/ml.

21. The method of claim 1, wherein said IFN-beta is present at a concentration of about 500 or about 810 μg/ml.

22. The method of claim 1, wherein said buffer is present at a concentration of about 5 mM to about 500 mM.

23. The method of claim 1, wherein said buffer is present at a concentration of about 10 mM or about 50 mM.

24. The method of claim 1, wherein said isotonicity agent is present at a concentration of about 0.5 mg/ml to about 500 mg/ml.

25. The method of claim 1, wherein said isotonicity agent is present at a concentration of about 55 mg/ml or about 150 mM or about 300 mM or about 600 mM.

26. The method of claim 1, wherein said surfactant is polysorbate 20 and is present at a concentration of about 0.01 mg/ml to about 10 mg/ml.

27. The method of claim 26, wherein said polysorbate 20 is present at a concentration of about 0.5 mg/ml.

28. The method of claim 1, wherein said antioxidant is present at a concentration of about 0.01 mg/ml to about 5.0 mg/ml.

29. The method of claim 28, wherein said antioxidant is present at a concentration of about 0.12 mg/ml or about 0.24 mg/ml.

30. The method of claim 1, wherein said amino acid is present at a concentration of about 20 mg/ml to about 200 mg/ml.

31. The method of claim 30, wherein said amino acid is lysine and is present at a concentration of about 27 mg/ml or about 55 mg/ml or about 82 mg/ml or about 164 mg/ml.

32. The method of claim 30, wherein said amino acid is arginine and is present at a concentration of about 32 mg/ml or about 63 mg/ml.

33. The method of claim 1, wherein said bacteriostatic agent is present at a concentration of about 0.01 mg/ml to about 200 mg/ml.

34. The method of claim 33, wherein said bacteriostatic agent is present at a concentration of about 5 mg/ml or about 10 mg/ml.

35. The method of claim 1, wherein said incubation is performed for 10, 16, 18.5 or 24 hours.

36. The method of claim 35, wherein said incubation is performed for 24 hours.

37. The method of claim 1, wherein said IFN-beta is maintained at a pH range of 3.0 to 6.0.

38. The method of claim 37, wherein said pH is 4.7.

39. The method according to claim 37, wherein said pH is 3.8.

* * * * *

UNITED STATES PATENT AND TRADEMARK OFFICE
CERTIFICATE OF CORRECTION

PATENT NO. : 7,858,082 B2
APPLICATION NO. : 11/597982
DATED : December 28, 2010
INVENTOR(S) : Amer Jaber It is certified that error appears in the above-identified patent and that said Letters Patent is hereby corrected as shown below:

Column 2,
Lines 26-27, "166 amino acid" should read --166 amino acids--.

Column 5,
Line 38, "others problems" should read --other problems--.

Column 6,
Line 26, "before that the final" should read --before the final--.

Column 8,
Line 1, "ethylenediaminetetraacefic" should read --ethylenediaminetetraacetic--.

Column 10,
Line 2, ""Whole"" should read --"whole"--.
Line 51, "but is not" should read --but are not--.

Column 23,
Line 9, "29 C" should read --29° C.--.
Line 47, "After 4 f/T" should read --After 4 F/T--.

Column 24,
Line 4, "After 4 f/T" should read --After 4 F/T--.
Table 13, Column "Sample", Row 3, "29c, 29C," should read --29 C., 29 C.,--.

Column 30,
Line 50, "tubes containing 130 gr bulk)" should read --tubes (containing 130 gr bulk)--.

Column 42,
Line 30, "(109.39 Mannitol/liter." should read --(109.39g Mannitol/liter).--.

Signed and Sealed this
Twenty-second Day of March, 2011

David J. Kappos
*Director of the United States Patent and Trademark Office*

Column 43,
Line 16, "filter washed" should read --filter was washed--.

Column 47,
Table 27, Column "5", Row 2, "93.8 (1.5" should read --93.8 (1.5)--.
Line 66, "Tween 20" should read --TWEEN 20--.

Column 48,
Line 26, "were then transfer" should read --were then transferred--.
Line 40, "4. Benzylalcohol and TWEEN 20. The embodiments" should read
   --4. Benzylalcohol and TWEEN 20.
The embodiments--.

Column 49,
Line 25, "at any stages" should read --at any stage--.

Column 50,
Line 29, "ultracentrigufation" should read --ultracentrifugation--.

Column 51,
Line 41, "centrepieces" should read --centerpieces--.

Column 52,
Line 28, "IFN-ε-1a" should read --IFN-β-1a--.

Column 54,
Line 15, "microliter" should read --microtiter--.
Line 53, "IFN-β1a" should read --IFN-β-1a--.

Column 55,
Line 22, "IFN-β1a" should read --IFN-β-1a--.
Lines 31-32, "table 34 below" should read --table 31 below--.
Line 55, "heights×1100" should read --heights ×100--.
Line 65, "IFN-β1a" should read --IFN-β-1a--.

Column 56,
Line 41, "at 101° C." should read --at 10° C.--.